United States Patent [19]

Chang et al.

[11] Patent Number: 5,410,026

[45] Date of Patent: * Apr. 25, 1995

[54] METHOD FOR REFOLDING INSOLUBLE, MISFOLDED INSULIN-LIKE GROWTH FACTOR-1 INTO AN ACTIVE CONFORMATION

[75] Inventors: Judy Y. Chang; Nancy C. McFarland, both of Hillsborough; James R. Swartz, Menlo Park, all of Calif.

[73] Assignee: Genentech, Inc., South San Francisco, Calif.

[*] Notice: The portion of the term of this patent subsequent to Feb. 22, 2011 has been disclaimed.

[21] Appl. No.: 161,044

[22] Filed: Dec. 2, 1993

Related U.S. Application Data

[63] Continuation of Ser. No. 808,451, Dec. 6, 1991, Pat. No. 5,288,931.

[51] Int. Cl.⁶ ................. C12N 15/00; C07K 7/04
[52] U.S. Cl. .................... 530/408; 530/399; 530/350; 530/409; 530/422; 530/412
[58] Field of Search ............. 530/399, 350, 408, 409, 530/422, 825, 826, 412; 435/69.1, 172.3; 930/10

[56] References Cited

U.S. PATENT DOCUMENTS

| | | | |
|---|---|---|---|
| 4,511,502 | 4/1985 | Builder et al. | 530/408 |
| 4,511,503 | 4/1985 | Olson et al. | 530/422 |
| 4,512,922 | 4/1985 | Jones et al. | 530/408 |
| 4,518,526 | 5/1985 | Olson | 530/408 |
| 4,572,798 | 2/1986 | Koths et al. | 530/312 |
| 4,620,948 | 11/1986 | Builder et al. | 530/419 |
| 4,652,630 | 3/1987 | Bentle et al. | 530/420 |
| 4,705,848 | 11/1987 | Yang et al. | 530/399 |
| 4,923,967 | 5/1990 | Bobbitt et al. | 530/399 |
| 4,985,544 | 1/1991 | Yokoo et al. | 530/399 |
| 5,019,500 | 5/1991 | Ueda et al. | 435/69.1 |
| 5,288,931 | 2/1994 | Chang | 530/399 |

FOREIGN PATENT DOCUMENTS

| | | |
|---|---|---|
| 0128733 | 12/1984 | European Pat. Off. |
| 0130166 | 1/1985 | European Pat. Off. |
| 0135094 | 3/1985 | European Pat. Off. |
| 0196056 | 10/1986 | European Pat. Off. |
| 0219814 | 4/1987 | European Pat. Off. |
| 0264074 | 4/1988 | European Pat. Off. |
| 0286345 | 10/1988 | European Pat. Off. |
| 0288451 | 10/1988 | European Pat. Off. |
| 0361830 | 4/1990 | European Pat. Off. |
| 0433225 | 6/1991 | European Pat. Off. |
| 62-190199 | 8/1987 | Japan . |
| WO8503949 | 9/1985 | WIPO . |
| WO8805821 | 8/1988 | WIPO . |
| WO8808003 | 10/1988 | WIPO . |
| WO8808849 | 11/1988 | WIPO . |
| WO8902465 | 3/1989 | WIPO . |
| WO8910976 | 11/1989 | WIPO . |
| WO9102807 | 3/1991 | WIPO . |
| WO92012993 | 8/1992 | WIPO . |
| WO8605809 | 10/1996 | WIPO . |

OTHER PUBLICATIONS

Raschdorf et al., "Location of disulphide Bonds in Human Insulin–like Growth Factors (IFGs) Synthesized by Recombinant DNA Technology", *Biomedical and Environmental Mass Spectrometry*, 16:3–8, (1988).

Schein et al., "Formation of Soluble Recombinant Proteins in *Escherichia Coli* is Favored by Lower Growth Temperature", *Bio/Technology*, 6:291–294, (1988).

Mizukami et al., "Production of Active Human Interferon-β in *E. coli*, I. Preperential Production by Lower Culture Temperature", *Biotechnology Letters* 8(9):605–610, (1986).

(List continued on next page.)

*Primary Examiner*—Garnette D. Draper
*Assistant Examiner*—Marianne Porta Allen
*Attorney, Agent, or Firm*—Janet E. Hasak

[57] ABSTRACT

A method for refolding insoluble, improperly folded IGF-I is provided, wherein the IGF-I, precipitated from prokaryotic host cells, is concurrently solubilized, unfolded, and refolded into a biologically active conformation in a single buffer. The buffer contains reducing agent and chaotropic agent to solubilize the IGF-I at concentrations sufficiently low to allow solubilization and refolding to occur. Also provided is a triple-protease deficient *E. coli* host suitable for use in the process.

22 Claims, 20 Drawing Sheets

OTHER PUBLICATIONS

Snyder, "Free Energy Relationships for Thiol–Disulfide Interchange Reactions between Charged Molecules in 50% Methanol", *The Journal of Biological Chemistry*, 259(12):7468–7472, (1984).

Halenbeck, "Renaturation and Purification of Biologically Active Recombinant Human Macrophage Colony–Stimulating Factor Expressed in *E. coli*", *Bio/Technology* 7:710–715, (1989).

Tsuji, "Characterization of Disulfide Bonds in Recombinant Porteins: Reduced Human Interleukin 2 in Inclusion Bodies and Its Oxidative Refolding", *Biochemistry*, 26:3129–3134 (1987).

George et al., "High–Level Expression in *Escherichia coli* of Biologically Active Bovine Growth Hormone", 273–281, DNA 4(4):273–281, (1985).

Gill et al., "Recombinant Chicken and Bovine Growth Hormones Accelerate Growth in Aquacultured Juvenile Pacific Salmon Oncorhynchus Kisutch", *Bio/Technology*, 3:643–646, (1985).

Sekine et al., "Cloning and expression of cDNA for salmon growth hormone in *Escherichia coli*", *Proc. Natl. Acad.* 82:4306–4310, (1985).

Green, "Cheddar cheesemaking with recombinant calf chymosin synthesized in *Escherichia coli*", *Journal of Dairy Research*, 52:281–286, (1985).

Marston, "The purification of eukaryotic polypeptides synthesized in *Escherichia coli*", *Biochem. J.*, 240:1–12, (1986).

Boss, "Assembly of functional antibodies from immunoglobulin heavy and light chains synthesized in *E. coli*", *Nucleic Acids Research*, 12:3791–3806 (1984).

Cabilly, "Generation of antibody activity from immunoglobulin polypeptide chains produced in *Escherichia coli*", *Pro. Natl. Acad. Sci.*, 81:3273–3277, (1984).

Marston et al., "Purification of Calf Prochymosin (Prorennin) Synthesized in *Escherichia Coli*", *Bio/Technology*, 2:800–804 (1984).

Hoppe et al., "Preparation of Biologically Active Platelet–Derived Growth Factor Type BB from a Fusion Protein Expressed in *Escherichia coli*", *Biochemistry*, 28:2956–2960, (1989).

Bowden, "Structure and Morphology of Protein Inclusion Bodies in *Escherichia Coli*", *Bio/Technology*, 9:725–730, (1991).

Mitraki et al., "Protein Folding Intermediates and Inclusion Body Formation", Bio/Technology, 7:690–697, (1989).

Marston et al., "Solubilization of Protein Aggregates", *Methods in Enzymology*, 182:264–276, (1986).

Wetzel, "Enhanced Folding and Stabilization of Proteins by Suppression of Aggregation In Vitro and In Vivo", *Protein Engineering–A Practical Approach*, 1–40, (1991).

Obukowicz et al., "Secretion and export of IGF–1 in *Escherichia coli* strain JM101", *MGG, Springer–Verlag* 215:19–25, (1988).

Wong et al., "Expression of secreted insulin–like growth factor–1 in *Escherichia coli*", 193–203, Gene, 68 1988.

Saito et al., "Direct Expression of a Synthetic Somatomedin C Gene in *Escherichia coli* by Use of a Two–Cistron System", *J. Biochem.* 101:1281–1288, (1987).

Schulz et al., "Increased Expression in *Escherichia coli* of a Synthetic Gene Encoding Human Somatomedin C after Duplication and Fusion", *Journal of Bacteriology* 169:5385–5392, (1987).

Saito, et al., "Production and Isolation of Recombinant Somatomedin C", *J. Biochem*, 101:123–134, (1987).

Niwa, et al., "Chemical Synthesis, Cloning and Expression of Genes for Human Somatomedin C (Insulin–like Growth Factor I) and $^{59}$Val–Somatomedin C", *Annals New York Academy of Sciences* 469:31–52, (1983).

Samuelsson et al., "Facilitated in Vitro Refolding of Human Recombinant Insulin–Like Growth Factor I Using A Solubilizing Fusion Partner", *Bio/Technology*, 9;363–366, (1991).

Buell et al., "Optimizing the expression in *E. coli* of a synthetic gene encoding somatomedin–C IGF–1", *Nucleic Acids Research*, 13:1923–1938, (1985).

Chang et al., "Folding of IGF–1", *Abstract paper, Amer. Chem. Soc.*, 203(117), (1992).

Hober et al., "Disulfide Exchange Folding of Insulin–like Growth Factor I", *Biochemistry*, 31:1749–1756, (1992).

Hejnaes et al., "Development of an optimized refoding process for recombinant Ala–Glu–IGF–1", 797–806 Protein Engineering, 31(8):5, (1992).

Cleland, "Impact of protein folding on biotechnology", *Protein Folding, In Vivo and In Vitro*, ACS Symopsium Series 526, p. 6, (1993).

Winkler et al., "Purification and Characterization of Recombinant Urokinase from *Escherichia Coli*", *Bio/Technology* 3:990–1000, (1985).

Iwai et al., "Direct identificatio of disulfide bond linkages in insulin–like growth factor I (IGF–I) by chemical synthesis", *Peptides, Chemistry, Structure, and Biology*, Proceedings of the 11th Amer. Peptide Symp., Jul. 9–14, 1989, 101–102, Rivier et al., eds., (1990).

Lineage of E.coli W3110 Strain 27C7

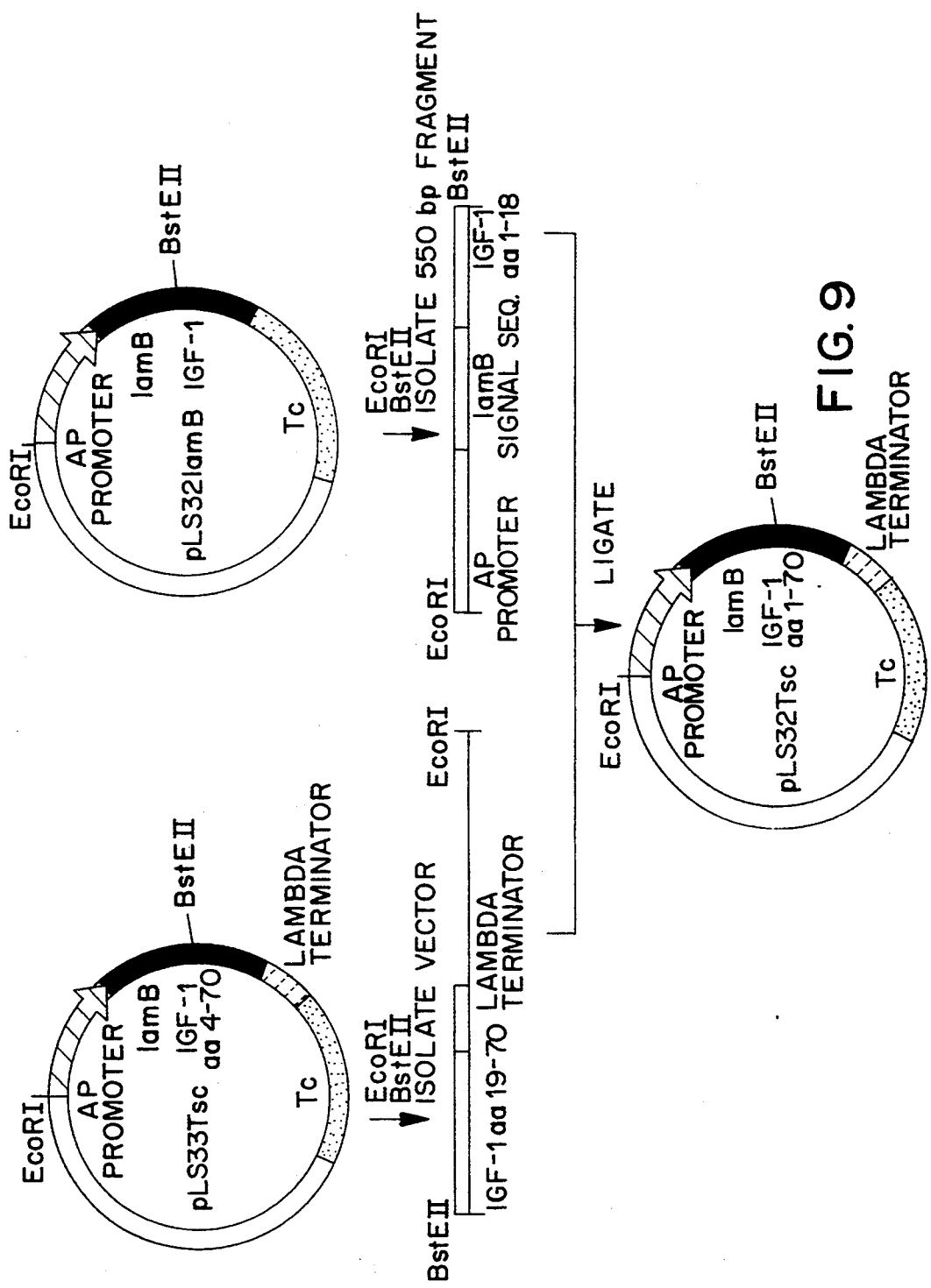

```
GAATTCAACT TCTCCATACT TTGGATAAGG AAATACAGAC ATGAAAAATC  50
TCATTGCTGA GTTGTTATTT AAGCTTGCCC AAAAAGAAGA AGAGTCGAAT 100
GAACTGTGTG CGCAGGTAGA AGCTTTGGAG ATTATCGTCA CTGCAATGCT 150
TCGCAATATG GCGCAAAATG ACCAACAGCG GTTGATTGAT CAGGTAGAGG 200
GGGCGCTGTA CGAGGTAAAG CCCGATGCCA GCATTCCTGA CGACGATACG 250
GAGCTGCTGC GCGATTACGT AAAGAAGTTA TTGAAGCATC CTCGTCAGTA 300
AAAAGTTAAT CTTTTCAACA GCTGTCATAA AGTTGTCACG GCCGAGACTT 350
ATAGTCGCTT TGTTTTTATT TTTTAATGTA TTTGTAACTA GTACGCAAGT 400
```

FIG. 10A

TCACGTAAAA AGGGTATCTA GAATTATG ATG ATT ACT CTG CGC 443
                                 Met Ile Thr Leu Arg
                                 -24             -20

AAA CTT CCT CTG GCG GTT GCC GTC GCA GCG GGC GTA ATG 482
Lys Leu Pro Leu Ala Val Ala Val Ala Ala Gly Val Met
                                             -10

TCT GCT CAG GCC ATG GCC GGT CCC GAA ACT CTG TGC GGT 521
Ser Ala Gln Ala Met Ala Gly Pro Glu Thr Leu Cys Gly
                            1

GCT GAA CTG GTT GAC GCT CTG CAG TTT GTT TGC GGT GAC 560
Ala Glu Leu Val Asp Ala Leu Gln Phe Val Cys Gly Asp
            10                                  20

CGT GGT TTT TAT AAC AAA CCC ACT GGT TAT GGT TCT 599
Arg Gly Phe Tyr Asn Lys Pro Thr Gly Tyr Gly Ser
                            30

FIG. 10B

```
TCT TCT CGT CGT GCT CCC CAG ACT GGT ATT GTT GAC GAA  638
Ser Ser Arg Arg Ala Pro Gln Thr Gly Ile Val Asp Glu
                        40

TGC TGC TTT CGT TCT TGC GAC CTG CGT CGT CTG GAA ATG  677
Cys Cys Phe Arg Ser Cys Asp Leu Arg Arg Leu Glu Met
            50

TAT TGC GCT CCC CTG AAA CCC GCT AAA TCT GCT TAG AAGCTC  719
Tyr Cys Ala Pro Leu Lys Pro Ala Lys Ser Ala AM*
    60                                      70

CTAACGCTCGG TTGCCGCCGG GCGTTTTTA TTGTTAA 757

Position Number -24 signifies the start of the lamB signal sequence.
Position NUmber   1 signifies the start of the IGF-I protein.
```

FIG. 10C

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 55 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GGTCCCGAAA  CTCTGTGCGG  TGCTGAACTG  GTTGACGCTC  TGCAGTTTGT      50

TTGCG                                                           55
```

( 2 ) INFORMATION FOR SEQ ID NO:2:

( i ) SEQUENCE CHARACTERISTICS:
        ( A ) LENGTH: 64 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
ACGTCCAGGG  CTTTGAGACA  CGCCACGACT  TGACCAACTG  CGAGACGTCA      50

AACAAACGCC  ACTG                                                64
```

( 2 ) INFORMATION FOR SEQ ID NO:3:

( i ) SEQUENCE CHARACTERISTICS:
        ( A ) LENGTH: 84 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

CTAGAATTAT GATGATTACT CTGCGCAAAC TTCCTCTGGC GGTTGCCGTC     50

GCAGCGGGCG TAATGTCTGC TCAGGCCATG GCCA     84

( 2 ) INFORMATION FOR SEQ ID NO:4:

( i ) SEQUENCE CHARACTERISTICS:
        ( A ) LENGTH: 84 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

TTAATACTAC TAATGAGACG CGTTTGAAGG AGACCGCCAA CGGCAGCGTC     50

GCCCGCATTA CAGACGAGTC CGGTACCGGT CTAG     84

( 2 ) INFORMATION FOR SEQ ID NO:5:

( i ) SEQUENCE CHARACTERISTICS:
        ( A ) LENGTH: 59 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

GGCCGGTCCC GAAACTCTGT GCGGTGCTGA ACTGGTTGAC GCTCTGCAGT     50

TTGTTTGCG     59

( 2 ) INFORMATION FOR SEQ ID NO:6:

( i ) SEQUENCE CHARACTERISTICS:
        ( A ) LENGTH: 60 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

CCAGGGCTTT GAGACACGCC ACGACTTGAC CAACTGCGAG ACGTCAAACA     50

AACGCCACTG     60

( 2 ) INFORMATION FOR SEQ ID NO:7:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( x i ) SEQUENCE DESCRIPTION: SEQ ID NO:7:

GGCCACTCTG TGCGGTGCTG AACTGGTTGA CGCTCTGCAG TTTGTTTGCG     50

( 2 ) INFORMATION FOR SEQ ID NO:8:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( x i ) SEQUENCE DESCRIPTION: SEQ ID NO:8:

TGAGACACGC CACGACTTGA CCAACTGCGA GACGTCAAAC AAACGCCACT     50

G     51

( 2 ) INFORMATION FOR SEQ ID NO:9:

( i ) SEQUENCE CHARACTERISTICS:
    ( A ) LENGTH: 39 bases
    ( B ) TYPE: nucleic acid
    ( C ) STRANDEDNESS: single
    ( D ) TOPOLOGY: linear ( x i ) SEQUENCE DESCRIPTION: SEQ ID NO:9:

```
CCTAACGCTC GGTTGCCGCC GGGCGTTTTT TATTGTTAA                                39
```

( 2 ) INFORMATION FOR SEQ ID NO:10:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( x i ) SEQUENCE DESCRIPTION: SEQ ID NO:10:

```
GGATTGCGAG CCAACGGCGG CCCGCAAAAA ATAACAATT                                39
```

( 2 ) INFORMATION FOR SEQ ID NO:11:

( i ) SEQUENCE CHARACTERISTICS:
        ( A ) LENGTH: 757 bases
        ( B ) TYPE: nucleic acid
        ( C ) STRANDEDNESS: single
        ( D ) TOPOLOGY: linear ( x i ) SEQUENCE DESCRIPTION: SEQ ID NO:11:

```
GAATTCAACT TCTCCATACT TTGGATAAGG AAATACAGAC ATGAAAAATC                    50
TCATTGCTGA GTTGTTATTT AAGCTTGCCC AAAAAGAAGA AGAGTCGAAT                   100
GAACTGTGTG CGCAGGTAGA AGCTTTGGAG ATTATCGTCA CTGCAATGCT                   150
TCGCAATATG GCGCAAAATG ACCAACAGCG GTTGATTGAT CAGGTAGAGG                   200
GGGCGCTGTA CGAGGTAAAG CCCGATGCCA GCATTCCTGA CGACGATACG                   250
GAGCTGCTGC GCGATTACGT AAAGAAGTTA TTGAAGCATC CTCGTCAGTA                   300
AAAAGTTAAT CTTTTCAACA GCTGTCATAA AGTTGTCACG GCCGAGACTT                   350
ATAGTCGCTT TGTTTTTATT TTTTAATGTA TTTGTAACTA GTACGCAAGT                   400
TCACGTAAAA AGGGTATCTA GAATTATGAT GATTACTCTG CGCAAACTTC                   450
CTCTGGCGGT TGCCGTCGCA GCGGGCGTAA TGTCTGCTCA GGCCATGGCC                   500
GGTCCCGAAA CTCTGTGCGG TGCTGAACTG GTTGACGCTC TGCAGTTTGT                   550
TTGCGGTGAC CGTGGTTTTT ATTTTAACAA ACCCACTGGT TATGGTTCTT                   600
CTTCTCGTCG TGCTCCCCAG ACTGGTATTG TTGACGAATG CTGCTTTCGT                   650
TCTTGCGACC TGCGTCGTCT GGAAATGTAT TGCGCTCCCC TGAAACCCGC                   700
TAAATCTGCT TAGAAGCTCC TAACGCTCGG TTGCCGCCGG GCGTTTTTA                    750
TTGTTAA                                                                  757
```

( 2 ) INFORMATION FOR SEQ ID NO:12:

( i ) SEQUENCE CHARACTERISTICS:
        ( A ) LENGTH: 94 amino acids
        ( B ) TYPE: amino acid
        ( D ) TOPOLOGY: linear ( x i ) SEQUENCE DESCRIPTION: SEQ ID NO:12:

```
Met Ile Thr Leu Arg Lys Leu Pro Leu Ala Val Ala Val Ala Ala
 1               5                  10                  15
Gly Val Met Ser Ala Gln Ala Met Ala Gly Pro Glu Thr Leu Cys
            20                  25                  30
```

| | | | | | | | | | | | | | |
|---|---|---|---|---|---|---|---|---|---|---|---|---|---|
| Gly | Ala | Glu | Leu | Val 35 | Asp | Ala | Leu | Gln | Phe 40 | Val | Cys | Gly | Asp Arg 45 |
| Gly | Phe | Tyr | Phe | Asn 50 | Lys | Pro | Thr | Gly | Tyr 55 | Gly | Ser | Ser | Ser Arg 60 |
| Arg | Ala | Pro | Gln | Thr 65 | Gly | Ile | Val | Asp | Glu 70 | Cys | Cys | Phe | Arg Ser 75 |
| Cys | Asp | Leu | Arg | Arg 80 | Leu | Glu | Met | Tyr | Cys 85 | Ala | Pro | Leu | Lys Pro 90 |
| Ala | Lys | Ser | Ala 94 | | | | | | | | | | |

METHOD FOR REFOLDING INSOLUBLE, MISFOLDED INSULIN-LIKE GROWTH FACTOR-1 INTO AN ACTIVE CONFORMATION

This is a continuation of application Ser. No. 07/808,451, filed Dec. 6, 1991, now U.S. Pat. No 5,288,931.

BACKGROUND OF THE INVENTION

1. Field of the Invention

This invention relates to an efficient method for refolding insulin-like growth factor-I (IGF-I) that has been produced in heterologous host cells and is present in these cells as clumps of insoluble protein.

2. Description of Related Art

The production of large quantities of relatively pure, biologically active polypeptides and proteins is important economically for the manufacture of human and animal pharmaceutical formulations, enzymes, and other specialty chemicals. For production of many proteins, recombinant DNA techniques have become the method of choice because large quantities of exogenous proteins can be expressed in bacteria and other host cells free of other contaminating proteins.

Producing recombinant protein involves transfecting host cells with DNA encoding the protein and growing the cells under conditions favoring expression of the recombinant protein. The prokaryote *E. coli* is favored as host because it can be made to produce recombinant proteins in high yields. Numerous U.S. patents on general bacterial expression of recombinant-DNA-encoded proteins exist, including U.S. Pat. Nos. 4,565,785 on a recombinant DNA molecule comprising a bacterial gene for an extracellular or periplasmic carrier protein and non-bacterial gene; 4,673,641 on coproduction of a foreign polypeptide with an aggregate-forming polypeptide; 4,738,921 on an expression vector with a trp promoter/operator and trp LE fusion with a polypeptide such as IGF-I; 4,795,706 on expression control sequences to include with a foreign protein; and 4,710,473 on specific circular DNA plasmids such as those encoding IGF-I.

Under some conditions, certain heterologous proteins expressed in large quantities from bacterial hosts are precipitated within the cells in dense masses, recognized as bright spots visible within the enclosure of the cells under a phase contrast microscope at magnifications down to 1000 fold. These clumps of precipitated proteins are referred to as "refractile bodies," and constitute a significant portion of the total cell protein. Brems et al., *Biochemistry*, 24: 7662 (1985). On the other hand, the clumps of protein may not be visible under the phase contrast microscope, and the expression "inclusion body" is often used to refer to the aggregates of protein whether visible or not under the phase contrast microscope.

Recovery of the protein from these bodies has presented numerous problems, such as how to separate the protein encased within the cell from the cellular material and proteins harboring it, and how to recover the inclusion body protein in biologically active form. The recovered proteins are often biologically inactive because they are folded into a three-dimensional conformation different from that of active protein. For example, recombinant IGF-I that has disulfide bonds formed between cysteine pairs different from the pairs found in the disulfide bonds of native IGF-I has significantly reduced biological activity. Raschdorf et al., *Biomedical and Environmental Mass Spectroscopy*, 16: 3–8 (1988). Misfolding occurs either in the cell or during the isolation procedure. Methods for refolding the proteins into the correct, biologically active conformation are essential for processing functional proteins.

Protein folding is influenced by the nature of the medium containing the protein and by a combination of weak attractive or repellent intramolecular forces involved in hydrogen bonding, ionic bonding, and hydrophobic interactions. When pairs of cysteine residues are brought into close proximity as the peptide backbone folds, strong covalent disulfide bonds form between cysteine residues, serving to lock the tertiary conformation in place. Refolding protocols have been designed to break incorrect disulfide bonds, block random disulfide bonding, and allow refolding and correct disulfide bonding under conditions favorable to the formation of active conformer.

It has been found that the soluble proportion of high-level expressed protein in *E. coli* has been dramatically increased by lowering the temperature of fermentation to below 30° C. A considerable fraction of various foreign proteins, i.e., human IFN-$\alpha$2, IFN-$\gamma$, and murine MX protein [Schein and Noteborn, *Bio/Technology*, 6: 291–294 (1988)] and human IFN-$\beta$ [Mizukami et al., *Biotechnol. Lett.*, 8: 605–610 (1986)], stayed in solution. This procedure represents an alternative to renaturation of proteins recovered from refractile bodies, but requires an expression system that is efficiently induced at temperatures below 30° C. The procedure is therefore not effective for all proteins.

One series of techniques for recovering active protein from inclusion bodies involves solubilizing the inclusion bodies in strongly denaturing solutions and then optionally exchanging weakly denaturing solutions for the strongly denaturing solutions (or diluting the strong denaturant), or using molecular sieve or high-speed centrifugation techniques. Such recovery methods, described, e.g., in U.S. Pat. Nos. 4,512,922; 4,518,256; 4,511,502; and 4,511,503, are regarded as being universally applicable, with only minor modifications, to the recovery of biologically active recombinant proteins from inclusion bodies. These methods seek to eliminate random disulfide bonding prior to coaxing the recombinant protein into its biologically active conformation through its other stabilizing forces.

In one such method, the denatured protein desired to be refolded is further purified under reducing conditions that maintain the cysteine moieties of the protein as free sulfhydryl groups by supplying a reducing agent throughout all the purification steps. This allows the protein to refold itself under the conditions of purification in the absence of incorrect disulfide bond formation. The reducing agent is then diluted into an aqueous solution to enable the refolded protein to form the appropriate disulfide bonds in the presence of air or some other oxidizing agent. This enables refolding to be easily incorporated into the overall purification process and works optimally for recombinant proteins having relatively uncomplicated tertiary structures in their biologically active forms.

In a second approach in this series, refolding of the recombinant protein takes place in the presence of both the reduced (R—SH) and oxidized (R—S—S—R) forms of a sulfhydryl compound. This allows free sulfhydryl groups and disulfides to be formed and reformed constantly throughout the purification process. The reduced and oxidized forms of the sulfhydryl compound are provided in a buffer having sufficient denaturing power that all of the intermediate conformations of the protein remain soluble in the course of the unfolding and refolding. Urea is suggested as a suitable buffer medium because of its apparent ability to act both as a sufficiently weak denaturing agent to allow the protein to approximate its correct conformation and as a sufficiently strong denaturant that the refolding intermediates maintain their solubility. This approach works best where the recombinant inclusion body proteins of interest have relatively uncomplicated folding patterns.

The third alternative in this series, used in more difficult refolding situations, is designed to break any disulfide bonds that may have formed incorrectly during isolation of the inclusion bodies and then to derivatize the available free sulfhydryl groups of the recombinant protein. This objective is achieved by sulfonating the protein to block random disulfide pairings, allowing the protein to refold correctly in weak denaturant, and then desulfonating the protein, which protocol favors correct disulfide bonding. The desulfonation takes place in the presence of a sulfhydryl compound and a small amount of its corresponding oxidized form to ensure that suitable disulfide bonds will remain intact. The pH is raised to a value such that the sulfhydryl compound is at least partially in ionized form to enhance nucleophilic displacement of the sulfonate.

These refolding protocols, while practical for their universal utility, have not been shown necessarily to be maximally efficient with, for example, recombinant IGF-I.

Enhancement of selected disulfide pairings by adding 50% methanol to buffer at low ionic strength has been reported by G. H. Snyder, *J. Biol. Chem.*, 259: 7468–7472 (1984). The strategy involves enhancing formation of specific disulfide bonds by adjusting electrostatic factors in the medium to favor the juxtaposition of oppositely charged amino acids that border the selected cysteine residues. See also Tamura et al., abstract and poster presented at the Eleventh American Peptide Symposium on Jul. 11, 1989 advocating addition of acetonitrile, DMSO, methanol, or ethanol to improve the production of the correctly folded IGF-I.

U.S. Pat. No. 4,923,967 and EP 361,830 describe a protocol for solubilizing and sulphitolysing refractile protein in denaturant, then exchanging solvent to precipitate the protein. The protein is resolubilized in denaturant and allowed to refold in the presence of reducing agent. The multiple steps required to achieve correct folding are time-consuming.

The recovery of the biological activity requires a carefully monitored renaturation procedure and may be very difficult depending on the protein in question. A number of publications have appeared that report refolding attempts for individual proteins that are produced in bacterial hosts or are otherwise in a denatured or non-native form. For example, formation of a dimeric, biologically active M-CSF after expression in *E. coli* is described in WO 88/8003 and by Halenbeck et al., *Biotechnology*, 7: 710–715 (1989). The procedures described involve the steps of initial solubilization of M-CSF monomers isolated from inclusion bodies under reducing conditions in a chaotropic environment comprising urea or guanidine hydrochloride, refolding achieved by stepwise dilution of the chaotropic agents, and final oxidation of the refolded molecules in the presence of air or a redox-system.

Reasonable recovery after renaturation has been reported for several proteins such as interleukin-2 (IL-2) [Tsuji et al., *Biochemistry*, 26: 3129–3134 (19871) WO 88/8849], growth hormone from various sources [George et al., *DNA*, 4: 273–281 (1984); Gill et al., *Bio/-Technology*, 3: 643–646 (1985); Sekine et al., *Proc. Natl. Acad. Sci. USA*, 82: 4306–4310 (1985); U.S. Pat. No. 4,985,544, the lattermost reference involving adding a denaturing agent and reducing agent to solubilize the protein, removing the reducing agent, oxidizing the protein, and removing the denaturing agent], prochymosin [Green et al., *J. Dairy Res.*, 52: 281–286 (1985)], urokinase [Winkler et al., *Bio/Technology*, 3: 990–1000 (1985)], somatotropin [U.S. Pat. No. 4,652,630, whereby urea is used for solubilization, and a mild oxidizing agent is then used for refolding], and tissue-plasminogen activator [Rudolph et al., in "623rd Biochem. Soc. Meeting," Canterbury (1987)]. See also Marston, *Biochemical J.*, 240: 1 (1986).

Where the efficiency of recovery has been reported, up to 40% active foreign protein has been obtained. See, e.g, Boss et al., *Nucl. Acids Res.*, 12: 3791–3806 (1984); Cabilly et al., *Proc. Natl. Acad. Sci. USA*, 81: 3273–3277 (1984); Marston et al., *Bio/Technology*, 2: 800–804 (1984); and Rudolph et al., supra. However, such yields may not be acceptable if the protein is costly to produce and must be made in commercial quantities.

Additional representative literature on refolding of nonnative proteins derived from different sources includes a report that IL-2 and interferon-$\beta$ (IFN-$\beta$) have been refolded using SDS for solubilization and $Cu^{+2}$ ions as oxidation promoters of the fully reduced proteins [U.S. Pat. No. 4,572,798]. A process for isolating recombinant refractile proteins as described in U.S. Pat. No. 4,620,948 involves using strong denaturing agents to solubilize the proteins, reducing conditions to facilitate correct folding, and denaturant replacement in the presence of air or other oxidizing agents to reform the disulfide bonds. The proteins to which the process can be applied include urokinase, human, bovine, and porcine growth hormone, interferon, tissue-type plasminogen activator, FMD coat protein, prorennin, and the src protein.

A method for renaturing unfolded proteins including cytochrome c, ovalbumin, and trypsin inhibitor by reversibly binding the denatured protein to a solid matrix and stepwise renaturing it by diluting the denaturant is disclosed in WO 86/5809. A modified monomeric form of human platelet-derived growth factor (PDGF) expressed in *E. coli* has been S-sulfonated during purification to protect thiol moieties and then dimerized in the presence of oxidizing agents to yield the active protein. Hoppe et al., *Biochemistry*, 28: 2956 (1989).

Additionally, EP 433,225 published 19 Jun. 1991 discloses a process for producing dimeric biologically active transforming growth factor-$\beta$ protein or a salt thereof wherein the denatured monomeric form of the protein is subjected to refolding conditions that include a solubilizing agent such as mild detergent, an organic, water-miscible solvent, and/or a phospholipid. See also Bowden et al., *Bio/Technology*, 9: 725 (1991) on $\beta$-lactamase cytoplasmic and periplasmic inclusion bodies, and Samuelsson et al., *Bio/Technology*, 9: 731 (1991) on refolding of human interferon-gamma mutants. For general review articles, see Marston, *Biochem. J.*, 240: 1–12 (1986); Mitraki and King, *Bio/Technology*, 7: 690 (1989); Marston and Hartley, *Methods in Enzymol.*, 182: 264–276 (1990); Wetzel, "Protein Aggregation In Vivo:

Bacterial Inclusion Bodies and Mammalian Amyloid," in *Stability of Protein Pharmaceuticals: In Vivo Pathways of Degradation and Strategies for Protein Stabilization*, Ahern and Manning (eds.), Plenum Press, 1991; and Wetzel, "Enhanced Folding and Stabilization of Proteins by Suppression of Aggregation In Vitro and In Vivo," in *Protein Engineering—A Practical Approach*, Rees, A. R. et al. (eds.), IRL Press at Oxford University Press, Oxford, 1991.

Several literature references exist on the production of IGF-I in bacteria. These include EP 128,733 published 19 Dec. 1984 and EP 135,094 published 27 Mar. 1985, which address expression of IGF-I in bacteria. EP 288,451 addresses use of lamB or ompF signal to secrete IGF-I in bacteria; Obukowicz et al., *Mol. Gen. Genet.*, 215: 19-25 (1988) and Wong et al., *Gene*, 68: 193-203 (1988) teach similarly. EP 286,345 discloses fermentation of IGF-I using a lambda promoter.

In addition, methods have been suggested for preparing IGF-I as a fusion protein. For example, EP 130,166 discloses expression of fusion peptides in bacteria, and EP 155,655 (U.S. Pat. No. 5,019,500) and EP 219,814 disclose a fusion of IGF-I with a protective polypeptide for expression in bacteria. EP 264,074 discloses a two-cistronic met-IGF-I expression vector with a protective peptide of 500-50,000 molecular weight [see also U.S. Pat. No. 5,028,531 and Saito et al., *J. Biochem.*, 101: 1281-1288 (1987)]. Other IGF-I fusion techniques that have been reported include fusion with protective peptide from which a rop gene is cut off [EP 219,814], IGF-I multimer expression [Schulz et al., *J. Bacteriol.*, 169: 5385-5392 (1987)], fusion of IGF-I with LH protein through a chemically cleavable methionyl or tryptophan residue at the linking site [Saito et al., *J. Biochem.*, 101: 123-134 (1987)], and fusion with superoxide dismutase [EP 196,056]. Niwa et al., *Ann. NY Acad. Sci.*, 469: 31-52 (1986) discusses the chemical synthesis, cloning, and successful expression of genes for IGF-I fused to another polypeptide.

These methods utilizing fusion proteins, however, generally require a relatively long leader sequence and are directed to improving expression of the inclusion body protein, not to improving refolding of the denatured recombinant protein. Int. Pub. No. WO 91/02807 published 7 Mar. 1991 describes a method for refolding recombinant IGF-I that involves cloning the IGF-I gene with a positively charged leader sequence prior to transfecting the DNA into the host cell. The additional positive charge on the amino terminus of the recombinant IGF-I allows correct refolding when the solubilized protein is stirred for 2-16 hours in denaturant solution. Following refolding, the leader sequence is cleaved and the active recombinant protein is purified. This multistep process is burdensome, requiring additional materials and effort to clone a heterologous leader sequence in front of the IGF-I gene and then to remove the leader sequence from the purified protein. Additionally, the 30-50% yield of active conformer, using this method, is unremarkable.

Another method for facilitating in vitro refolding of recombinant IGF-I involves using a solubilized affinity fusion partner consisting of two IgG-binding domains (ZZ) derived from staphylococcal protein A. Samuelsson et al., *Bio/Technology*, 9: 363 (1991). While this method, which uses the protein A domain as a solubilizer of misfolded and multimeric IGF-I, results in higher yields of IGF-I without the use of denaturing agents or redox chemicals, it involves the extra steps of fusing onto the IGF-I gene a separate gene and removing the polypeptide encoded by that gene after expression of the fusion gene.

As regards the bacterial hosts that may be utilized for fermentation processes, WO 88/05821 published 11 Aug. 1988 discloses a method of isolating a mutant strain of *E. coli* having a defective periplasmic protease. WO 89/02465 published 23 Mar. 1989 discloses a process for production of a polypeptide comprising direct expression of the polypeptide in bacterial host cells using an inducible expression system in combination with a protease-deficient bacterial host system, including a host deficient in two proteases. WO 85/03949 published 12 Sep. 1985 discloses bacterial cell strains carrying specific mutations within their DNA sequences that cause the cells to exhibit a reduced capacity for degrading foreign products due to reduced expression of cellular proteases, with a htpR lon *E. coli* host exemplified. WO 89/10976 published 16 Nov. 1989 discloses protease-deficient gram-positive bacteria and their use as host organisms for producing recombinant proteins. In addition, Buell et al., *Nucl. Acids Res.*, 13: 1923-1938 (1985) discloses use of an *E. coli* host mutated at lon and htpR to produce IGF-I.

There is a need in the art for a simple, one-step, efficient protocol for refolding insoluble, misfolded IGF-I into the correct conformation so that the biological activity of the IGF-I can be restored.

Accordingly, it is an object of the present invention to provide such procedure for reactivating, in one step, misfolded IGF-I recovered from inclusion bodies formed in prokaryotic cells, allowing for recovery of biologically active IGF-I at low cost and high yield.

It is a particularly preferred object to provide a one-step solubilization and refolding procedure to reactivate misfolded recombinant IGF-I precipitated in the periplasmic space of bacterial host cells.

It is another object to provide protease-deficient *E. coli* hosts that are particularly suited for the solubilization and refolding process herein.

These and other objects will be apparent to those of ordinary skill in the art.

Summary of the Invention

Accordingly, the present invention provides a method for reactivating insoluble, misfolded IGF-I present in prokaryotic host cells by isolating the insoluble IGF-I and incubating it in an alkaline buffered solution comprising no more than 3M chaotropic agent and the minimum amount of reducing agent necessary for solubilization, under conditions of IGF-I concentration and incubation temperature and time so that unfolding and refolding to the active conformation take place concurrently with solubilization in the same buffer.

Preferably, the IGF-I is isolated by exposing the cells to a buffer of suitable ionic strength to solubilize most host polypeptides, but not the insoluble IGF-I, disrupting the cells to form a soluble and an insoluble fraction, and isolating the insoluble IGF-I fraction as by centrifugation.

The use of minimal amounts of chaotropic agent and reducing agent allows breaking of disulfide bonds so that misfolded conformers can correctly refold under mild conditions. In addition, the entire solubilization and refolding process takes place in one simple incubation step without the need to remove any chaotropic or reducing agent or to add redox buffer or other agent.

In another aspect, the invention provides an *E. coli* strain having the complete genotype tonAΔ ptr3 phoA-ΔE15 Δ(argF-lac)169 in a W3110 background, and the strains additionally having the genotype ompTΔ or ompTΔ degP41. The invention further provides for such strains that are transformed with a vector encoding IGF-I. These strains can be utilized in the process of this invention.

BRIEF DESCRIPTION OF THE DRAWINGS

FIG. 9 depicts the construction of pLS32Tsc from pLS33Tsc and pLS32lamB.

FIGS. 10A 10B and 10C depict the nucleotide sequence of the expression cassette and amino acid sequence encoding the lamB signal sequence and the IGF-I in plasmid pLS32Tsc.

DESCRIPTION OF THE PREFERRED EMBODIMENTS

A. Definitions

Figure 1:
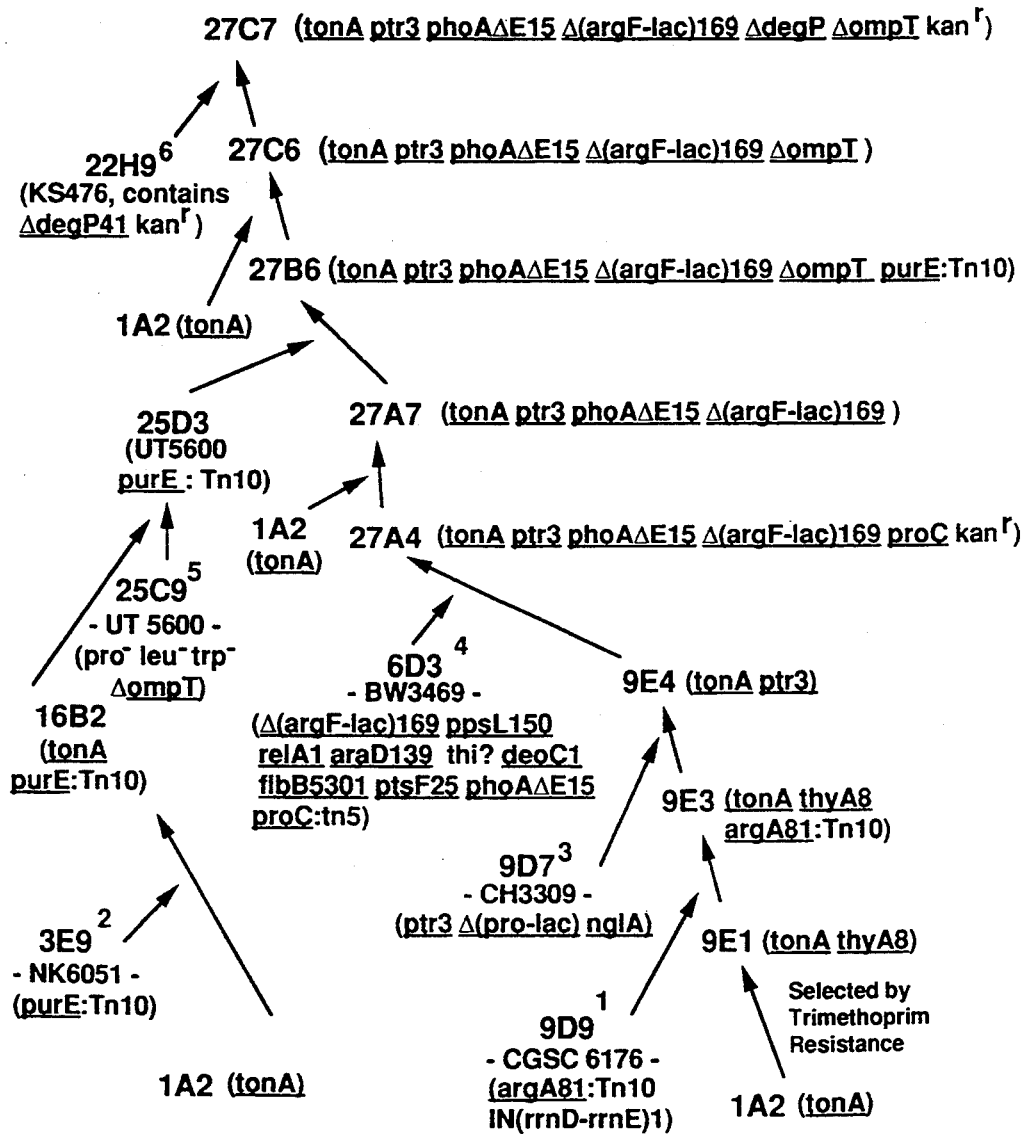
FIG. 1 illustrates the lineage of *E. coli* W3110 host strain 27C7.

As used herein, "insoluble, misfolded IGF-I" refers to precipitated or aggregated IGF-I that is contained within the periplasm of prokaryotic host cells, or is otherwise prokaryotic host cell associated, and assumes a biologically inactive conformation with mismatched or unformed disulfide bonds. The insoluble IGF-I is preferably, but need not be, contained in refractile bodies, i.e., it may or may not be visible under a phase contrast microscope.

The term "conformers" refers to polypeptides recovered from inclusion bodies containing recombinant IGF-I that differ only in intramolecular disulfide bonding. IGF-I is 70 amino acids long and has six cysteine residues that form intramolecular disulfide bonds. The correct, active conformer has disulfide bonds between amino acid residues C6–C48, C47–C52, and C18–C61. The other main polypeptide recovered from such inclusion bodies is a misfolded, biologically inactive conformer having disulfide bonds between amino acid residues C6–C47, C48–C52, and C18–C61.

As used herein, "chaotropic agent" refers to a compound that, in a suitable concentration in aqueous solution, is capable of changing the spatial configuration or conformation of proteins through alterations at the surface thereof so as to render the IGF-I up to about 90% soluble in the aqueous medium. The alterations may occur by changing, e.g., the state of hydration, the solvent environment, or the solvent-surface interaction. The concentration of chaotropic agent will directly affect its strength and effectiveness. A strong chaotropic agent is a compound which, in solution, will effectively unfold a protein present in the solution. The unfolding will be relatively extensive, but reversible. A moderate chaotropic agent is a compound which, in solution, permits partial folding of a protein from whatever contorted conformation the protein has assumed through intermediates soluble in the solution, into the spatial conformation in which it finds itself when operating in its active form under endogenous or homologous physiological conditions.

As used herein, "IGF-I" refers to insulin-like growth factor from any species, including bovine, ovine, porcine, equine, and preferably human, in native sequence or in variant form and recombinantly produced. Preferred herein, IGF-I is cloned, and expressed, e.g., by the process described in EP 128,733 published Dec. 19, 1984.

As used herein, "reducing agent" refers to a compound or material which, in a suitable concentration in aqueous solution, maintains sulfhydryl groups in the reduced state and reduces disulfide intra- or intermolecular bonds.

As used herein, "buffered solution" refers to a solution which resists changes in pH by the action of its acid-base conjugate components.

As used herein, "hydrophobic agent" refers to a nonpolar solute that, when added to aqueous solution, increases the hydrophobicity of the solution.

B. Modes for Carrying Out the Invention

Insoluble, misfolded IGF-I is isolated from host cells in a suitable isolation buffer by any appropriate technique, e.g., one involving exposing the cells to a buffer of suitable ionic strength to solubilize most host proteins, but in which aggregated IGF-I is substantially insoluble, disrupting the cells so as to release the inclusion bodies and make them available for recovery by, for example, centrifugation. This technique is well known, and is described, for example, in U.S. Pat. No.

4,511,503. Briefly, the cells are suspended in the buffer (typically at pH 5 to 9, preferably about 6 to 8, using an ionic strength of about 0.01 to 2M, preferably 0.1 to 0.2M). Any suitable salt, including NaCl, is useful to maintain a sufficient ionic strength value. The cells, while suspended in this buffer, are then disrupted by lysis using techniques commonly employed such as, for example, mechanical methods, e.g., a Manton-Gaulin press, a French press, or a sonic oscillator, or by chemical or enzymatic methods.

Examples of chemical or enzymatic methods of cell disruption include spheroplasting, which entails the use of lysozyme to lyse the bacterial wall [H. Neu et al., *Biochem. Biophys. Res. Comm.*, 17: 215 (1964)], and osmotic shock, which involves treatment of viable cells with a solution of high tonicity and with a cold-water wash of low tonicity to release the polypeptides [H. Neu et al., *J. Biol. Chem.*, 240(9): 3685–3692 (1965)]. A third method, described in U.S. Pat. No. 4,680,262 issued Jul. 14, 1987, involves contacting the transformed bacterial cells with an effective amount of a lower alkanol having 2 to 4 carbon atoms for a time and at a temperature sufficient to kill and lyse the cells.

After the cells are disrupted, the suspension is typically centrifuged at low speed, generally around 500 to 15,000×g, preferably about 12,000×g, in a standard centrifuge for a sufficient time that depends on volume and centrifuge design, usually about 10 minutes to 0.5 hours, preferably 12,000×g for 10 minutes. The time may be substantially reduced in a disc stack type centrifuge. The resulting pellet contains substantially all of the insoluble IGF-I fraction, but if the cell disruption process is not complete, it may also contain intact cells or broken cell fragments. Completeness of cell disruption can be assayed by resuspending the pellet in a small amount of the same buffer solution and examining the suspension with a phase contrast microscope if the IGF-I is contained in refractile bodies. The presence of broken cell fragments or whole cells indicates that further sonication or other means of disruption is necessary to remove the fragments or cells and the associated non-refractile polypeptides. After such further disruption, if required, the suspension is again centrifuged and the pellet recovered, resuspended, and reexamined. The process is repeated until visual examination reveals the absence of broken cell fragments in the pelleted material or until further treatment fails to reduce the size of the resulting pellet.

The above process can be employed whether the insoluble protein is intracellular or in the periplasmic space. The preferred conditions given herein for isolating IGF-I are directed particularly to inclusion bodies precipitated in the periplasmic space.

The isolated insoluble, misfolded IGF-I is then incubated in alkaline buffer containing the minimum amount of chaotropic agent and reducing agent necessary substantially to solubilize the IGF-I and allow refolding. This incubation takes place under conditions of IGF-I concentration, incubation time, and incubation temperature that will allow solubilization of IGF-I, and unfolding and refolding of IGF-I to occur concurrently in the alkaline buffer.

Measurement of the degree of solubilization of the IGF-I in the buffer is suitably carried out by turbidity determination, by analyzing IGF-I fractionation between the supernatant and pellet after centrifugation on reduced SDS gels, by protein assay (e.g., the Bio-Rad protein assay kit), or by HPLC. The degree of refolding is suitably determined by the RIA titer of IGF-I or by HPLC analysis using e.g., a Vydac C18 column, with increasing RIA titer or correctly folded IGF-I peak size directly correlating with increasing amounts of correct, biologically active IGF-I conformer present in the buffer. The incubation is carried out to maximize the ratio of correctly folded IGF-I conformer to misfolded IGF-I conformer recovered, as determined by RIA or HPLC.

The pH range of the buffer typically is at least about 7.5, with the preferred range being 7.5–10.5. Examples of suitable buffers that will provide a pH within this latter range include CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N.-Cyclohexylamino]ethanesulfonic acid), TRIS (Tris[hydroxymethyl]aminomethane), and sodium acetate. The preferred buffer herein is CAPSO at about pH 8.5–10.5.

Examples of suitable reducing agents include DTT, BME, and cysteine. The minimal amount of reducing agent to be present in the buffer will depend mainly on the type of reducing agent and chaotropic agent, the type and pH of the buffer employed, the amount of oxygen entrained in or introduced to the solution, and the concentration of the IGF-I in the buffer. For example, with 0.5–1.5 mg/ml IGF-I in a buffered solution at pH 7.5–10.5 containing 1–4M urea, the DTT concentration is at about 1–8 mM and the BME concentration is at about 0.2–2 mM. The preferred reducing agent is DTT at about 2–4 mM, BME at about 1–2 mM, or cysteine at about 2–4 mM.

Chaotropic agents suitable for practicing this invention include, e.g., urea and salts of guanidine or thiocyanate, more preferably urea, guanidine hydrochloride, or sodium thiocyanate. The amount of chaotropic agent minimally necessary to be present in the buffer is no more than about 3 molar. The preferred chaotropic agent herein is urea at about 1.5–2.5M, more preferably at about 2M, or guanidine hydrochloride at about 1–3M.

The conditions of incubation of the insoluble, misfolded IGF-I will generally be such that substantial or complete solubilization of the IGF-I will take place, as well as maximal refolding. The exact conditions will depend on, e.g., the pH of the buffer and the types and concentrations of chaotropic and reducing agents. The reaction temperature must not be so high as to denature the IGF-I, and is therefore generally about 10°–40° C. The incubation will generally be carried out for at least about 1 hour to effect concurrent solubilization and refolding. The reaction is preferably carried out at about 15°–37° C., more preferably 20°–30° C., for at least about 1 hour, more preferably 2–12 hours.

The concentration of the IGF-I in the buffered solution must be such that the IGF-I will be substantially solubilized and the ratio of correctly folded to misfolded conformer recovered will be maximized, as determined by HPLC. The exact amount to employ will depend, e.g., on the concentrations and types of other ingredients in the buffered solution, particularly the IGF-I concentration, reducing agent, and the pH of the buffer. For example, the concentration of IGF-I may be increased at least three-fold without decreasing the ratio of correct to misfolded conformer if the concentration of reducing agent, e.g. DTT, is concurrently increased, to maintain a ratio of IGF-I: DTT of from about 0.11 to 0.2. The preferred concentration of IGF-I (resulting in the maximum yield of correctly folded conformer) is in the range of 0.5–5.5 mg per ml, more preferably 1.5–5.0 mg/ml.

Addition of a hydrophobic agent to the buffer is generally suitable for increasing the yield of correctly folded conformer. Examples of suitable hydrophobic agents include organic solvents such as methanol, ethanol, DMSO (dimethylsulfoxide), and acetonitrile. Methanol and ethanol are effective as about 5–20% solutions, more preferably about 20%, and DMSO is effective as about a 40–50% solution.

Host cells that express the recombinant IGF-I abundantly in the form of inclusion bodies are prokaryotic cells. Suitable prokaryotes include bacteria, preferably eubacteria, such as Gram-negative or Gram-positive organisms, for example, *E. coli*, Bacilli such as *B. subtilis*, Pseudomonas species such as *P. aeruginosa, Salmonella typhimurium*, or *Serratia marcescens*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Strain W3110 is a preferred host or parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strains 1A2, 27A7, 27B4, and 27C7, described further below.

The invention will be more fully understood by reference to the following examples which are intended to illustrate the invention but not to limit its scope. All literature and patent citations are expressly incorporated by reference.

EXAMPLE I

Production and Isolation of rhIGF-I And Test for Its Solubility in Tris Buffer i. Construction of host cell strain 27C7

The host used to produce recombinant human IGF-I in the fermentation described herein was a derivative of *E. coli* W3110, designated 27C7. The complete genotype of 27C7 is tonA$\Delta$ ptr3 phoA$\Delta$E15 $\Delta$(argF-lac)169 ompT$\Delta$ degP41kan$^r$. The derivation of strain 27C7 is diagrammed in FIG. 1 and is described below. Strain 27C7 was deposited on Oct. 30, 1991 in the American Type Culture Collection as ATCC No. 55,244.

Strain 27C7 was constructed in several steps using techniques involving transductions with phage P1kc, derived from P1 (J. Miller, *Experiments in Molecular Genetics* (Cold Spring Harbor, N.Y.: Cold Spring Harbor Laboratory, 1972)), and transposon genetics [Kleckner et al., *J. Mol. Bio.*, 116: 125–159 (1977)]. The starting host used was *E. coli* K12 W3110, which is a K12 strain that is F-,$\lambda$- [Bachmann, *Bact. Rev.*, 36: 525–557 (1972); Bachman, "Derivatives and Genotypes of Some Mutant Derivatives of *Escherichia coli* K-12," p. 1190–1219, In F. C. Niedhardt et al., ed., *Escherichia coli and Salmonella typhimurium: Cellular and Molecular Biology*, vol. 2, American Society for Microbiology, Washington, D.C. (1987) ].

Figure 2A:
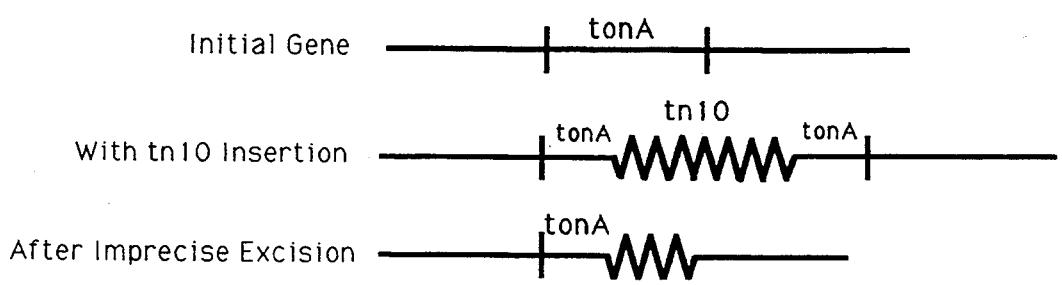
FIGS. 2A and 2B depict the schemes for the mutation of the tonA and phoA genes, respectively, in *E. coli* strain W3110.
Figure 2B:
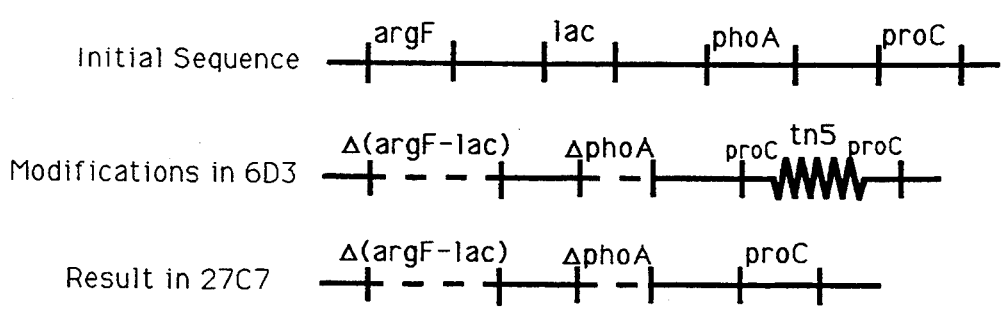
Figure 3:
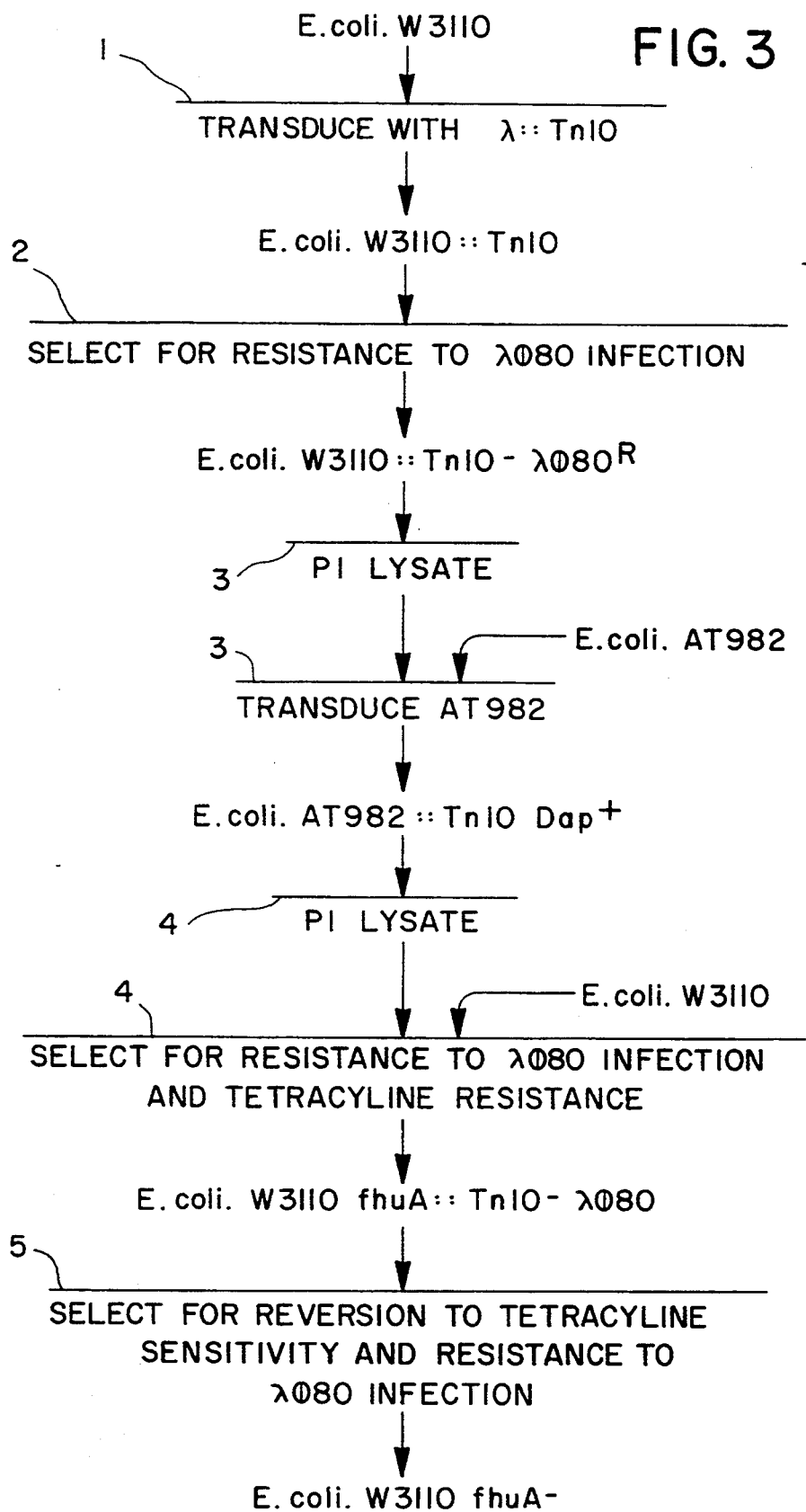
FIG. 3 depicts in detail the construction for the elimination of the tonA gene from W3110.

First, the tonA gene (fhuA) [Kadner et al., *J. Bact.,* 143: 256–264 (1980), Bachmann, *Microbiol. Rev.,* 47: 180–230 (1983), Bachman, "Linkage Map of *Escherichia coli* K-12," edition 7, p. 807–876, in F. C. Niedhardt et al., ed., "*Escherichia coli and Salmonella tryphimurium: Cellular and Molecular Biology*, Vol. 2, American Society for Microbiology, Washington, D.C., 1987] was deleted from W3110 by the insertion and subsequent imprecise excision of a Tn10 transposon into the tonA gene. This construction is diagrammed in FIGS. 2B and 3.

In the first step of this procedure, *E. coli* W3110 was transduced with $\lambda$::Tn1O to generate a Tn10 hop pool of *E. coli* W3110 [Kleckner et al., *J. Mol. Biol.*, supra].

The *E. coli* W3110::Tn10 hop pool was grown in L broth at 37° C. to a cell density of about $1 \times 10^9$/ml. A total of 0.5 ml of the culture was centrifuged and the pellet was resuspended in 0.2 ml of a $\lambda$phi80 lysate containing $7.0 \times 10^9$ pfu. The phage was allowed to adsorb for 30 minutes at 37° C. The suspension was then spread on EMB plates supplemented with tetracycline (15 $\mu$g/ml). After an overnight incubation at 37° C., the colonies were pooled in 3 ml of L broth, grown overnight at 37° C., washed twice, and resuspended in L broth. A bacteriophage P1kc lysate was made on this culture [Miller, J. H., *Experiments in Molecular Biology*, supra, page 304].

*E. coli* AT982 (no. 4546, *E. coli* Genetic Stock Center, New Haven, Conn.) was transduced to tetracycline resistance by this P1kc lysate. Transductants were selected on L broth plates supplemented with tetracycline (15 $\mu$g/ml) and 40 $\mu$g/ml diaminopimelic acid (dap). The resulting transductants were screened for tetracycline resistance and the regeneration of the dap gene (dap+, tet$^R$). Transductants with the dap+, tet$^R$ genotype were then tested for $\lambda$phi80 resistance.

P1kc lysates were then made on several dap+, tet$^R$, $\lambda$phi80-resistant strains. The lysates were used to transduce *E. coli* W3110 to tetracycline resistance. The transductants were screened and selected for $\lambda$phi80 resistance.

Tetracycline-sensitive isolates were selected from the W3110 tonA::Tn10-$\lambda$phi80R transductants. [Maloy and Nunn, *J. Bacteriol.,* 145: 1110 (1981)]. These isolates were checked for $\lambda$phi80 resistance and tetracycline sensitivity after single colony purification.

DNA was isolated from several tetracycline-sensitive $\lambda$phi80-resistant mutants and digested with SstII. The Sst-II-digested DNA was characterized by the Southern blot procedure using radioactively labeled and SstII-digested $\lambda$::Tn10 DNA as a probe to determine if the Tn10 had been excised [Davis et al., *Advanced Bacterial Genetics* (Cold Spring Harbor Laboratory, New York, 1980)]. One of the tetracycline-sensitive isolates was shown to have lost two of the Tn10 hybridization bands as compared to the hybridization between DNA from the $\lambda$::Tn10 and the parental W3110 tonA::Tn10$\lambda$-phi80R. A third hybridization band had an altered mobility, indicating that a deletion caused by the imprecise excision of Tn10 had occurred.

SDS-gel electrophoresis of outer membrane preparations from the strain with an imprecise Tn10 excision revealed that the band assumed to be the protein encoded by tonA had an altered electrophoretic mobility as compared to the wild-type protein encoded by the tonA gene. The resulting protein was non-functional as a $\lambda$phi80 phage receptor protein. A second independent strain that also had undergone imprecise excision of Tn10 showed no protein encoded by tonA on the SDS gel.

Neither of these strains demonstrated reversion to tetracycline resistance or to $\lambda$phi80 susceptibility, indicating that there was an imprecise excision of all or part of the Tn10 transposon together with either a partial or complete deletion of the tonA gene. Thus, the protein encoded by the tonA gene (MW 78,000) was eliminated from the outer membrane, rendering the W3110 tonA strain resistant to several bacteriophages. The resulting strain, designated 1A2, is resistant to bacteriophages T1 and φ80.

The ptr3 gene [Cheng et al., *J. Bacteriol.,* 140: 125-130 (1979)]was introduced into strain 1A2 as follows. First, the thyA8 mutation was isolated in 1A2 by selecting for trimethoprim resistance to form strain 9E1. Then the argA81::tn10 locus was transported from 9D9 (obtained from B. Bachman, *E. coli* Genetic Stock Center, New Haven, Conn.) into 9E1 by transduction with phage P1kc to form 9E3. The ptr3 locus is between thyA8 and argA81. Transduction with P1 phage grown on a ptr3 mutant [9D7, *J. Bact.,* 140: 125 (1979)] resulted in the introduction of the ptr3 mutation simultaneously with the conversion of thyA8 and argA81::Tn10 to wild-type loci. This strain, designated 9E4, lacks the periplasmic protease III. The conclusion that the ptr3 mutation is included in 9E4 is supported by strongly improved IGF-I accumulation in the resultant strain.

Then, two more deletion mutations, phoAΔE15 [Sarthy et al., *J. Bacteriol.,* 145: 288-292 (1981) ]and Δ(argF-lac)169 [Schweizer and Boos, *Mol. Gen. Genet.,* 192: 293-294 (1983)], were simultaneously transferred into 9E4 by genetic linkage to a kanamycin-resistance transposon inserted into a proline biosynthetic gene (proC::Tn5), contained in 6D3, obtained from Professor Barry Wanner, Purdue University. This construction is diagrammed in FIG. 2B.

The transposon was eliminated by selecting for a prototrophic (pro+) isolate on glucose minimal agar plates after P1 transduction with 1A2. The introduction of the phoA mutation eliminates alkaline phosphatase expression and was recognized as transductants that form white colonies on glucose-minimal agar plates with 0.2 mM phosphate and 20 mg/l 5-bromo-4-chloro-3-indolyl phosphate. Likewise, the Δ(argF-lac)169 mutation causes the loss of the enzyme beta-galactosidase (a lac-phenotype) and results in cells that form white colonies on MacConkey-1% lactose agar plates. The resultant strain was designated 27A7.

The ompT deletion [Earhart et al., *FEBS Microbiol. Lett.,* 6: 277-280 (1979)] was introduced into 27A7 by P1 cotransduction. It should be noted that this ompT deletion extends into the neighboring ent gene cluster which codes for the attachment proteins for colicins B and D. First, a linked Tn10 insertion in the purE gene was inserted next to the ompT deletion using conventional transduction techniques [intermediates 3E9 (similar strain obtainable from Dr. Carol Gros, University of Wisconsin), 16B2, 25C9 (*J. Bacter.,* 153: 1104-1106 (1983)), and 25D3]. Then, the purE::Tn10 was transduced into 27A7. Finally, this strain was transduced to purine prototrophy to remove the transposon. Maintenance of the ompTΔgenotype was confirmed by colicin B resistance in the resultant strain, which is designated 27C6. This strain lacks the outer membrane protease VII.

Finally, an additional periplasmic protease mutation, degP41kan[r] [Strauch et al., *J. Bacteriol.,* 171: 2689-2696 (1989); Harvard Medical School]was transduced into strain 27C6 by standard techniques. This mutation was constructed in vitro by replacing a section of the degP gene with the kanamycin gene. This is not a transposon but allows for selection of the deletion using kanamycin resistance.

This final strain, 27C7, has the following characteristics: it is phage resistant, lacks three proteases, fails to grow on lactose, and fails to produce alkaline phosphatase on the depletion of phosphate in the media, the same conditions that induce production of rhIGF-I.

ii. Description/Construction of Expression Plasmid pLS32Tsc

The secretion plasmid pLS32Tsc used to transform strain 27C7, contains the IGF-I gene. The transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamB signal sequence or alternatively the STII signal sequence. The majority of rhIGF-I is found in the cell periplasmic space. Plasmid pLS32Tsc confers tetracycline resistance upon the transformed host.

Plasmid pLS32Tsc was constructed in several steps using as intermediate plasmids pLS32, pAPlamB, pLS32lamB, pLS33lamB, and pLS33Tsc.

Step 1: pLS32

Figure 4:
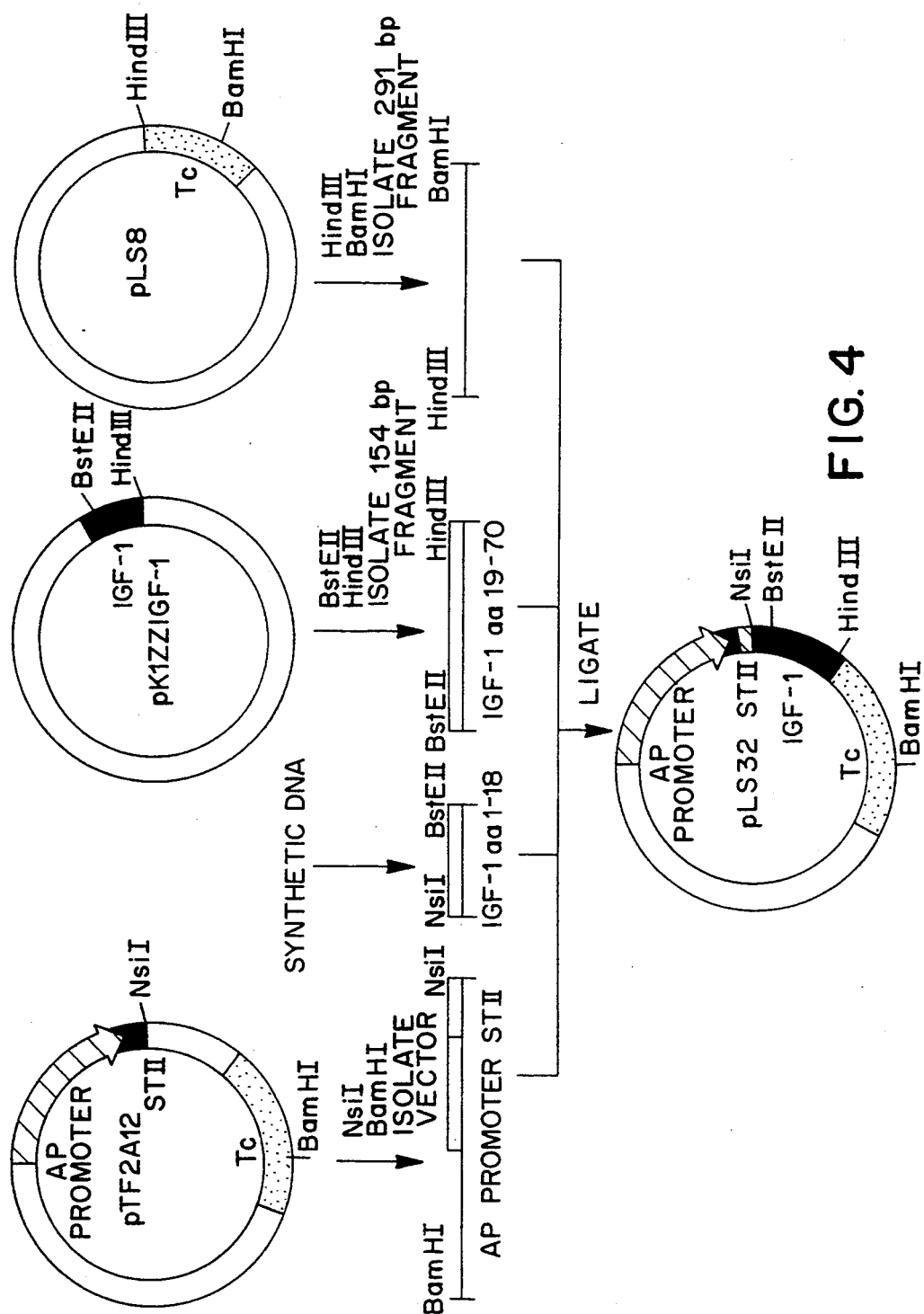
FIG. 4 depicts the construction of plasmid pLS32, an intermediate plasmid in preparing pLS32Tsc, which contains a gene encoding IGF-I.

The plasmid pLS32 results in the fusion of the IGF-I coding sequence to that of the heat-stable enterotoxin II (STII) signal sequence and was prepared by ligating together four DNA fragments as shown in FIG. 4. The first of these was the vector pTF2A12 [Paborsky et al., *Biochemistry,* 28: 8072-8077 (1989)]from which the small NsiI-BamHI fragment containing the tissue factor gene had been removed. The STII signal sequence is described by Picken et al., *Infect. Immun.,* 42: 269-275 (1983).

The second fragment was a 55-bp synthetic duplex encoding the first 18 amino acids of mature IGF-I. This duplex has the following sequence:

```
5'-GGTCCCGAAACTCTGTGCGGTGCT-
   GAACTGGTTGACGCTCT-
   GCAGTTTGTTTGCG-3'

3'-ACGTCCAGGGCTTTGAGACACGCCAC-
   GACTTGACCAACTGCGAGACGT-
   CAAACAAACGCCACTG-5'
```

(Sequence Identity Nos. 1 and 2, respectively)

The third piece in the ligation was a 154-bp BstEII-HindIII fragment from pK1ZZIGF-I encoding the remaining amino acids 19-70 of IGF-I. pK1ZZIGF-I is a kanamycin-resistant plasmid containing a lac promoter attached to a Protein A promoter attached to a Protein A signal, attached to two consensus Z regions from Protein A that bind IgGs and secrete proteins, fused using two codons encoding an Asn-Gly interface to a synthetic IGF-I gene and also containing an F region to give high copy number. This plasmid is similar to pZZ-IGF-I shown in FIG. 6 of and described in EP Pub. No. 230,869 published 5 Aug. 1987, where the ampicillin gene is replaced by a kanamycin gene.

The last fragment was a 291-bp HindIII-BamHI fragment from the plasmid pLS8. This last fragment is simply the coding sequence for the start of the tetracycline gene of pBR322 [Sutcliffe, *Cold Spring Harbor Symposia on Quantitative Biology,* 43: 77-90 (1978)]in which a HindIII restriction site was engineered immediately upstream of the methionine start codon.

The resulting plasmid, pLS32, efficiently expresses and secretes rhIGF-I to the media. The following two construction steps were made to replace the STII signal sequence with the lamB signal sequence, improving product yield.

Step 2: pAPlamB

Figure 5:
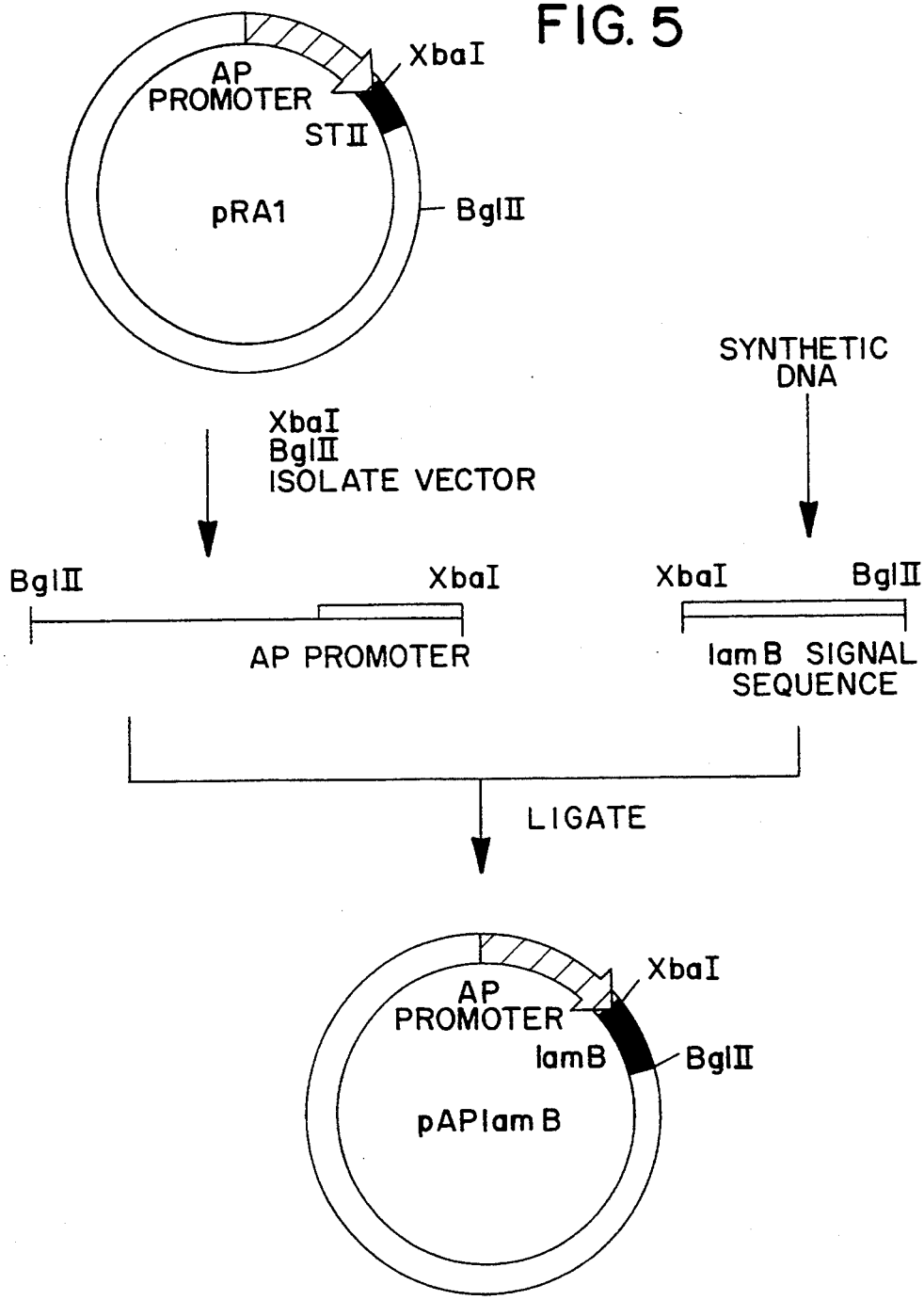
FIG. 5 depicts the construction of pAPlamB, another intermediate in preparing pLS32Tsc.

The plasmid pAPlamB was constructed as shown in FIG. 5 by ligating together two DNA fragments, and results in the placement of the lamB signal coding sequence downstream of the AP promoter and the trp Shine-Dalgarno sequence. Included in the ligation was the vector pRA1 in which the small XbaI-BglII fragment had been removed. This plasmid is a derivative of phGH1 [Chang et al., Gene, 55: 189–196 (1987)], which latter plasmid contains the AP promoter, the STII signal, and DNA encoding hGH. pRA1 differs from phGH1 in that it contains DNA encoding relaxin A chain (the sequence of which is described in U.S. Pat. No. 4,758,516) rather than hGH and it contains a convenient BglII restriction site downstream of the promoter and ribosome binding site. The second piece in the ligation was a 80-bp synthetic DNA duplex with the following sequence, which encodes the lamB signal sequence, which has been described by Clement and Hofnung, Cell, 27: 507–514 (1981):

```
5'-CTAGAATTATGATGATTACTCTGC-
   GCAAACTTCCTCTGGCGGTTGCCGTC-
   GCAGCGGGCGTAATGTCTGCTCAGG-
   CCATGGCCA-3'

3'-TTAATACTACTAATGAGACGCGTTT-
   GAAGGAGACCGCCAACG-
   GCAGCGTCGCCCGCATTACAGAC-
   GAGTCCGGTACCGGTCTAG-5'
```

(Sequence Identity Nos. 3 and 4, respectively)

Step 3: pLS32lamB

Figure 6:
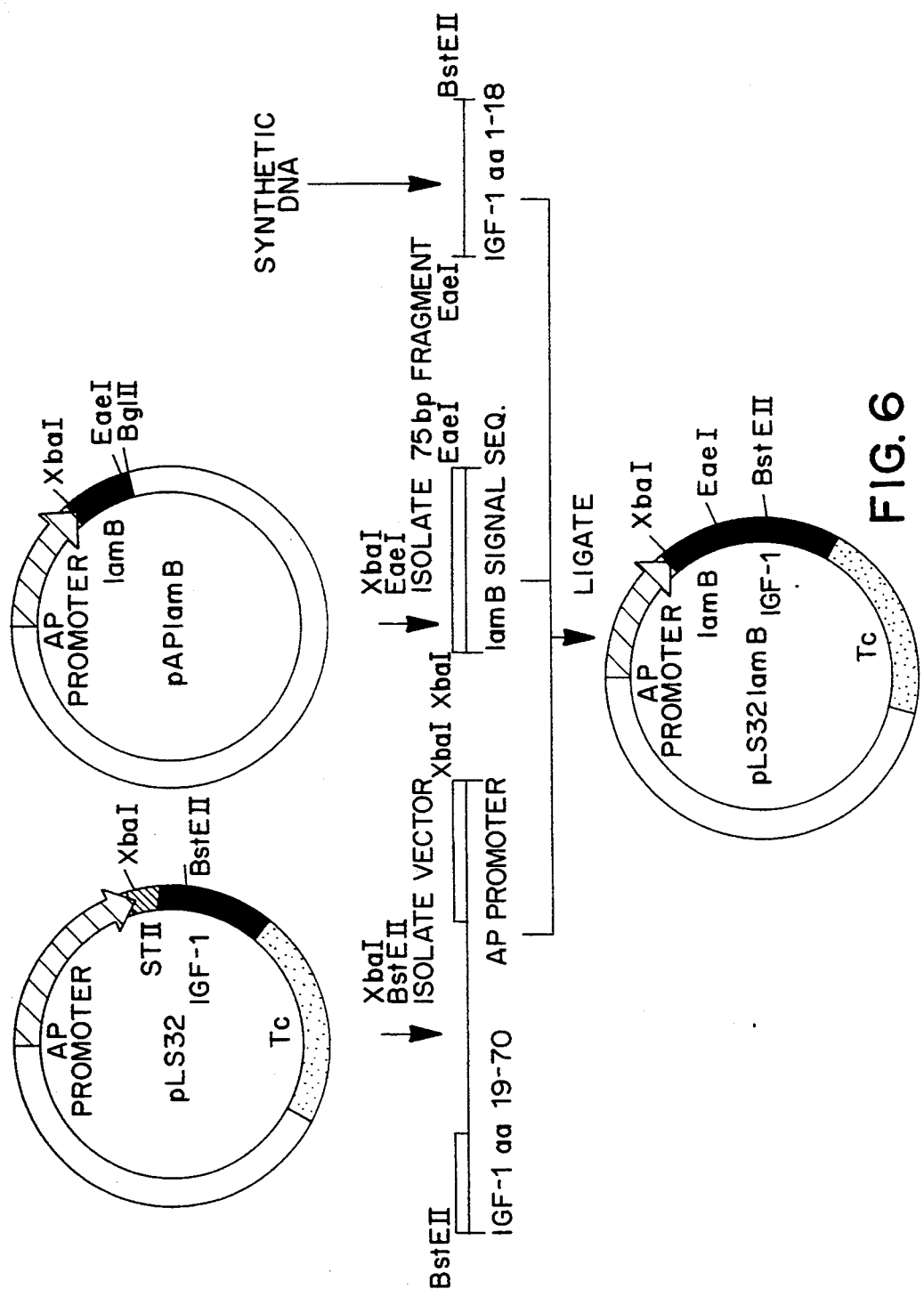
FIG. 6 depicts the construction of pLS32lamB, still another intermediate in the construction of pLS32Tsc.

The plasmid pLS32lamB results in the fusion of the lamB signal sequence to the IGF-I coding region and was constructed as shown in FIG. 6 by the ligation of three DNA fragments. The first of these was the vector pLS32 in which the small XbaI-BstEII fragment had been removed. The second was a 75-bp XbaI-EaeI fragment from pAPlamB encoding the lamB signal sequence. The third was a 55-bp synthetic DNA duplex encoding the first 18 amino acids of mature IGF-I, and having the following sequence:

```
5'-
  GGCCGGTCCCGAAACTCTGTGCGGTGC-
  TGAACTGGTTGACGCTCT-
  GCAGTTTGTTTGCG-3'

3'-CCAGGGCTTTGAGACACGCCACGACTT-
  GACCAACTGCGAGACGTCAAACAAACG-
  CCACTG-5'
```

(Sequence Identity Nos. 5 and 6, respectively)

The following steps introduce into the plasmid the transcriptional terminator. These plasmid changes resulted in an improved product yield.

Step 4: pLS33lamB

Figure 7:
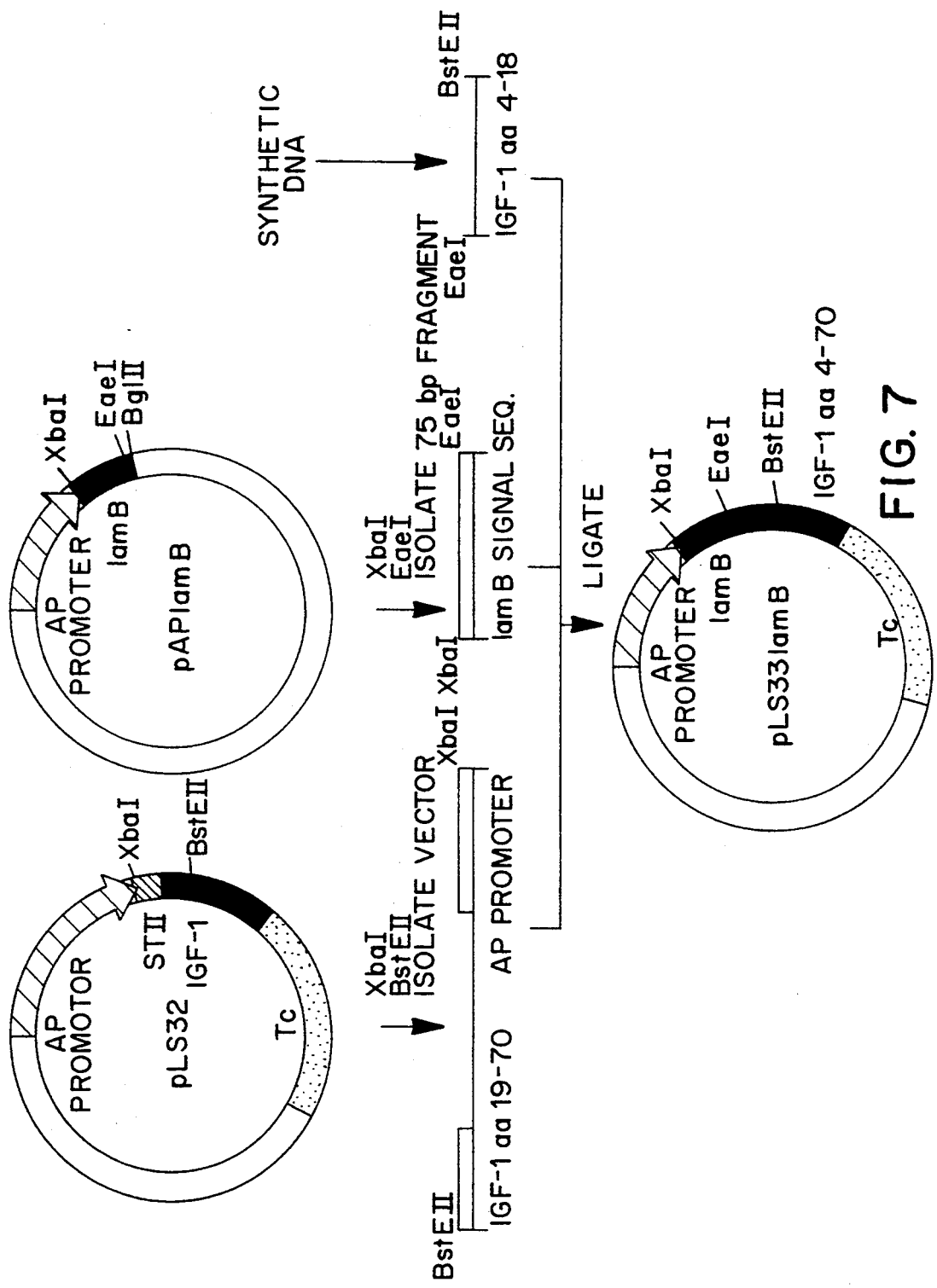
FIG. 7 depicts the construction of pLS33lamB, yet another intermediate in the preparation of pLS32Tsc.

The plasmid pLS33lamB is an intermediate in the preparation of pLS32Tsc and was constructed as shown in FIG. 7 by ligating together three DNA fragments. The first of these was the vector pLS32 in which the small XbaI-BstEII fragment had been removed. The second was a 75-bp XbaI-EaeI fragment from pAPlamB encoding the lamB signal sequence. The third was a 46-bp synthetic DNA duplex with the following sequence:

```
5'-GGCCACTCTGTGCGGTGCT-
   GAACTGGTTGACGCTCT-
   GCAGTTTGTTTGCG-3'

3'-TGAGACACGCCACGACTTGACCAACTG-
   CGAGACGTCAAACAAACGCCACTG-5'
```

(Sequence Identity Nos. 7 and 8, respectively) The above sequence encodes amino acids 4–18 of mature IGF-I.

Step 5: pLS33Tsc

Figure 8:
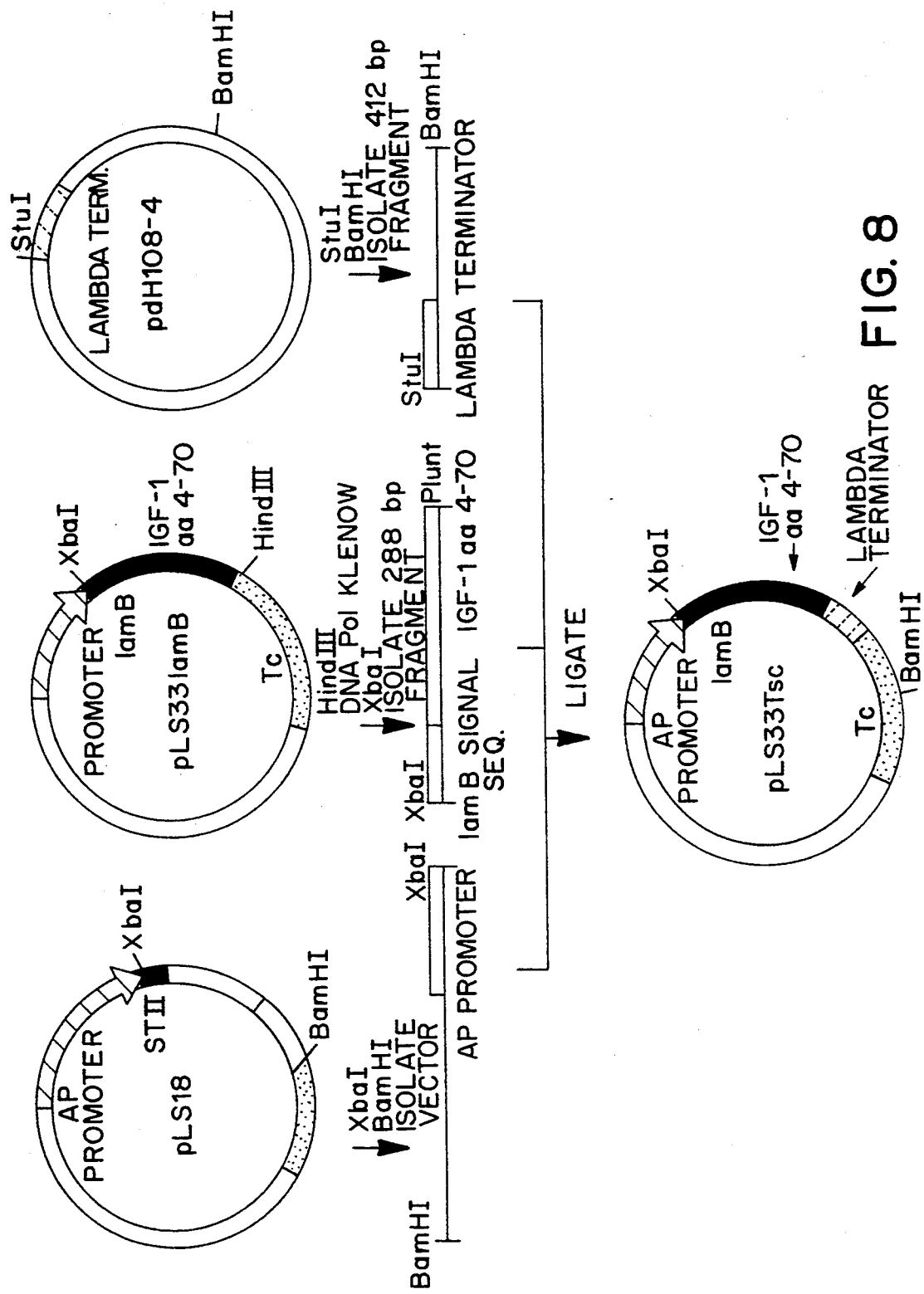
FIG. 8 depicts the construction of pLS33Tsc, yet another intermediate in the preparation of pLS32Tsc.

The plasmid pLS33Tsc results in the placement of the lambda $t_o$ transcriptional terminator immediately downstream of the IGF-I coding sequence. Three DNA fragments were ligated together as shown in FIG. 8 to construct this plasmid. The first piece was the vector pLS18 in which the small XbaI-BamHI fragment had been removed. pLS18 is a derivative of phGH1 [Chang et al., supra]that contains DNA encoding human DNase (as disclosed in WO 90/07572 published Jul. 12, 1990) rather than hGH. phGH1 could be used to generate the same fragment. The second part of the ligation was a 288-bp XbaI-HindIII fragment from pLS33lamB in which the HindIII restriction site had been blunted by treatment with DNA polymerase I (Klenow). The third part of the ligation was a 412-bp StuI-BamHI fragment from the plasmid pdH108–4. This fragment contains the lambda $t_o$ transcriptional terminator [Scholtissek and Grosse, Nuc. Acids Res., 15: 3185 (1987)]and base pairs 2–375 of pBR322 [Sutcliffe, supra], wherein the base pairs 2–375 are downstream or 3' of the transcriptional terminator. The sequence of the terminator region of this fragment is as follows:

```
5'-
  CCTAACGCTCGGTTGCCGCCGGGCGTT-
  TTTTATTGTTAA-3'

3'-GGATTGCGAGCCAACGGCGGCCC-
  GCAAAAAATAACAATT-5'
```

(Sequence Identity Nos. 9 and 10, respectively)

Step 6: pLS32Tsc

The final plasmid pLS32Tsc was constructed as shown in Fig. 9 by ligating together two DNA fragments. The first of these was the vector pLS33Tsc from which the small EcoRI-BstEII fragment had been removed. The second was a 550-bp EcoRI-BstEII fragment from pLS32lamB containing the AP promoter, trp Shine-Dalgarno, and the coding sequence for the lamB signal sequence fused to the first 18 amino acids of IGF-I. The resulting plasmid was analyzed by restriction endonuclease digestion. The entire promoter and coding sequence was verified by DNA sequencing, with the sequence being given in FIG. 10 (Sequence Identity No. 11(DNA) and 12(amino acid).

iii. Fermentation and Recovery Procedure

Competent E. coli 27C7, cells were transformed with pLS32Tsc by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

One transformed colony was used to inoculate sterile LB broth containing 20 mg/L tetracycline. The flask culture was incubated at 35°–39° C. until the optical density at 550 nm reached approximately 1.0. Sterile DMSO was added to the culture to give a final concentration of DMSO of 10% (v/v). Aliquots of 1-2 mL were dispensed into sterile vials and stored at −60° C. or below.

The fermentation process for producing rhIGF-I using 27C7/pLS32Tsc was performed in batches ranging in volume from 5 to 12 liters. At the end of the fermentation, cells were harvested by centrifugation.

A shake flask inoculum was prepared by inoculating approximately 500 ml of sterile LB medium containing tetracycline with the freshly thawed 1-2 ml culture vial described above. The shake flask was incubated at 35°-39° C. at 50-200 rpm for 7-12 hours. The shake flask was then used to inoculate a 15-liter fermentation vessel containing 5-9 liters of culture medium composed as follows:

| Ingredient | Quantity/Liter |
| --- | --- |
| glucose* | 250-350 g |
| ammonium sulfate | 2-6 g |
| ammonium hydroxide | as required to control pH 7.1 to 7.5 |
| sodium phosphate, monobasic dihydrate | 1-2 g |
| potassium phosphate, dibasic | 2-3 g |
| sodium citrate, dihydrate | 0.5-1.5 g |
| potassium chloride | 1-2 g |
| 25% Pluronic Polyol L61 | 0.2 ml initially and as needed to control foaming |
| magnesium sulfate, heptahydrate | 1-3 g |
| tetracycline HCl | 5-20 mg |
| yeast extract** | 5-15 g |
| NZ amine AS** | 5-20 g |
| isoleucine | 0-10 g |
| ferric chloride, heptahydrate | 10-30 mg |
| zinc sulfate, heptahydrate | 2-5 mg |
| cobalt chloride, hexahydrate | 2-5 mg |
| sodium molybdate, dihydrate | 2-5 mg |
| cupric sulfate, pentahydrate | 2-5 mg |
| boric acid | 0.5-2 mg |
| manganese sulfate, monohydrate | 1-3 mg |

* 2-5 g/L of glucose was added to the culture initially. The remainder was fed to the culture over the course of the fermentation at rates rapid enough to allow rapid growth during the initial part of the fermentation, but not so rapid as to cause the dissolved oxygen level to fall below 30% of air saturation levels during the latter portion of the fermentation (when significant cell mass has accumulated).
** Yeast extract and NZ amine AS can be added initially and/or fed throughout the fermentation.

The fermentation process was performed at 35°-39° C. at pH 7.1-7.5 for 24-48 hours. The agitation rate was set at 650-1000 rpm and the aeration rate at 0.7-1.5 volumes of air per volume of culture per minute. Production of IGF-I occurred after the phosphate in the medium was depleted. After the fermentation, the culture was chilled and then harvested by centrifugation. Harvested cells were resuspended in cell lysis buffer (approximately 4 g cell paste/100 ml) containing 25 mM Tris, pH 7.5, 5 mM EDTA, with 200 μg/ml hen egg white lysozyme, and sonicated at 4° C. for approximately 5 min. Cell lysates were centrifuged at 5,000 to 15,000×g at 4° C. for 10 min and the supernatant and pellet fractions were analyzed on reduced and nonreduced SDS gels.

iv. Results

A. Distribution of IGF-I

The reduced gel revealed that for whole cell lysates, approximately 10% of total cell protein is IGF-I, contained almost exclusively in the pellet fraction. On the non-reduced gel, the IGF-I band was nearly absent while numerous high molecular weight faint bands appeared, suggesting that the majority of cell-associated IGF-I is in a disulfide-linked, aggregated form.

B. Solubilization of IGF-I in Tris buffer

The refractile body material from a 4 ml OD cell pellet, isolated as described above, was solubilized in 100 μl of 25 mM Tris, pH 7.5, plus 5 mM EDTA and varying amounts of DTT and chaotropic agent (urea or guanidine chloride). Solubilization of the refractile particles was examined by observing the clearing of the refractile particle suspensions (i.e., the decrease in turbidity of the suspension) and was confirmed by centrifuging the samples and conducting Coomassie blue-stained PAGE gel analysis of the resulting supernatant and pellet fractions. The protein concentration in the supernatant (also an indication of solubility) was measured by the protein assay kit provided by BioRad (Richmond, CA). Supernatant was also assayed for IGF-I by radioimmunoassay (RIA). Refractile body protein was not soluble with either chaotropic agent alone or DTT alone; however, in combination, the protein was efficiently solubilized. See Table 1.

TABLE 1

Solubilization with Minimal Chaotropic Agent and DTT in Tris Buffer

| Chaotropic Agent (M) | DTT (mM) | Solubility* | IGF-I by RIA (μg/ml OD) |
| --- | --- | --- | --- |
| 0 agent | 0 | — | 0.05 |
| 0 urea | 10 | — | 0.00** |
| 2 urea | " | + | 0.47** |
| 4 urea | " | ++++ | 1.09** |
| 6 urea | " | ++++ | 1.10** |
| 8 urea | " | ++++ | 1.11** |
| 4 urea | 1 | +++ | 0.53** |
| 6 urea | " | +++ | 1.81** |
| 8 urea | " | +++ | 0.69** |
| 2 urea | " | +++ | 0.72** |
| 2 urea | 2 | +++ | 0.10** |
| 2 urea | 3 | +++ | 0.08** |
| 2 urea | 4 | ++++ | 0.04** |
| 4 urea | 0 | — | 0.06 |
| 4 urea | 1 | +++ | 0.57 |
| 4 urea | 2 | ++++ | 0.08 |
| 4 urea | 4 | ++++ | 0.06 |
| 4 urea | 6 | ++++ | 0.08 |
| 4 urea | 8 | ++++ | 0.15 |
| 4 urea | 10 | ++++ | 0.13 |
| 3 urea | 10 | +++ | 0.19 |
| 2 urea | 0 | — | 0.06 |
| 4 urea | 0 | — | 0.08 |
| 6 urea | 0 | — | 0.10 |
| 8 urea | 0 | — | 0.11 |
| 8 urea | 10 | ++++ | 0.05 |
| 2 GuCl*** | 0 | — | 0.14 |
| 4 GuCl | 0 | — | 0.12 |
| 6 GuCl | 0 | — | 0.10 |
| 6 GuCl | 10 | ++++ | 0.08 |

*"—" designates not soluble; "++++" is the most soluble.
Refolded for five hours; no "" designates refolded for two hours.
***GuCl designates guanidine hydrochloride.

Apparently, complete solubilization was attained with 2M urea/4 mM DTT or at least 4M urea and at least 2 mM DTT. It was found that the RP-HPLC peak area corresponding to the correct, authentic form of IGF-I accounts for all of the RIA titer, suggesting that when soluble IGF-I becomes RIA recognizable, it acquires a correctly folded conformation. Only minor amounts of IGF-I were detectable by RIA, even in the completely solubilized protein samples, indicating that the tertiary structure of the protein solubilized under these conditions was not the same as that of authentic IGF-I.

At pH 7.5 or less, Tris buffer does not result in significant yield of correctly folded IGF-I; however, correct refolding occurs in Tris buffer above pH 8.0. See FIG.

11A, where various buffers are compared, described more fully in Example III, Section C.

EXAMPLE II

Test for Solubility of IGF-I in Acetate Buffer and for Refolding and Effect of Incubation Temperature A. Solubilization and refolding of IGF-I in sodium acetate buffer Cell lysates were prepared as above through the cell harvesting step. Refractile body protein was solubilized in 100 mM sodium acetate (NaOAc) pH 8.2 containing 100 mM NaCl and in varying concentrations of urea and DTT.

At least 70% of the refractile body protein was soluble with 2M urea and DTT at 2 mM or greater. Optimal solubility and IGF-I titer was obtained with 2M urea, 2–4 mM DTT. See Table 2. In the absence of DTT, both solubility and IGF-I titer were insignificant.

TABLE 2

| Effect of Urea and DTT Concentrations at pH 8.2 | | | | | |
|---|---|---|---|---|---|
| Urea (M) | DTT (mM) | Solubility | IGF-I by RIA (μg/ml OD) | Protein (mg/ml) | % Refold |
| 0 | 0 | — | 0.01 | | |
| 1 | 10 | ++ | 0.05 | | |
| 2 | 0 | — | 0.12 | | |
| " | 1 | ++ | 4.76 | | |
| " | 2 | +++ | 5.43 | | |
| " | 4 | +++(+) | 5.85 | | |
| " | 6 | ++++ | 2.05 | | |
| " | 8 | ++++ | 0.88 | | |
| " | 10 | ++++ | 0.27 | | |
| 1 | 0 | — | 0.08 | | |
| " | 1 | ++ | 4.61 | | |
| " | 2 | +++ | 3.74 | | |
| " | 4 | +++ | 0.52 | | |
| 2 | 0 | — | 0.12 | 0.17 | 3 |
| " | 1 | ++ | 5.82 | 0.62 | 37 |
| " | 2 | ++++ | 6.88 | 1.22 | 22 |
| " | 4 | ++++ | 6.23 | 1.35 | 18 |
| 3 | 0 | — | 0.11 | | |
| " | 1 | ++ | 4.81 | | |
| " | 2 | +++ | 5.02 | | |
| " | 4 | +++ | 4.00 | | |
| 4 | 0 | — | 0.04 | | |
| " | 1 | −(+) | 0.15 | | |
| " | 2 | + | 0.26 | | |
| " | 4 | +++ | 0.13 | | |

In the presence of 1 or 2 mM DTT and 2M urea, varying the starting cell concentration (used to obtain refractile body protein) from 0.10 to 4.00 ml-OD indicated that the higher concentrations tested were more favorable for refolding only when 2 mM DTT was employed. See Table 3. Protein from 1–4 ml-OD of cell pellet was optimal.

TABLE 3

| Effect of IGF-I Concentration on Refolding | | | | | | |
|---|---|---|---|---|---|---|
| DTT (mM) | Starting Cells (ml-OD) | Solubility | RIA (μg/ml-OD) | Soluble Protein Concentration | | % Refold |
| | | | | (mg/ml) | (μg/ml OD) | |
| 1 | 0.10 | +++ | 9.4 | 0.07 | 71 | 13 |
| " | 0.25 | +++ | 11.8 | 0.22 | 86 | 14 |
| " | 0.50 | +++ | 15.2 | 0.33 | 65 | 46 |
| " | 1.00 | +++ | 8.9 | 0.33 | 33 | 27 |
| " | 4.00 | ++ | 9.2 | 1.08 | 27 | 34 |
| 2 | 0.10 | ++++ | 0.2 | 0.13 | 130 | 0.2 |
| " | 0.25 | ++++ | 0.1 | 0.30 | 121 | 0 |
| " | 0.50 | ++++ | 1.9 | 0.33 | 67 | 2.3 |
| " | 1.00 | ++++ | 11.8 | 0.52 | 52 | 23 |
| " | 4.00 | +++ | 8.2 | 1.35 | 34 | 24 |

Figure 12:
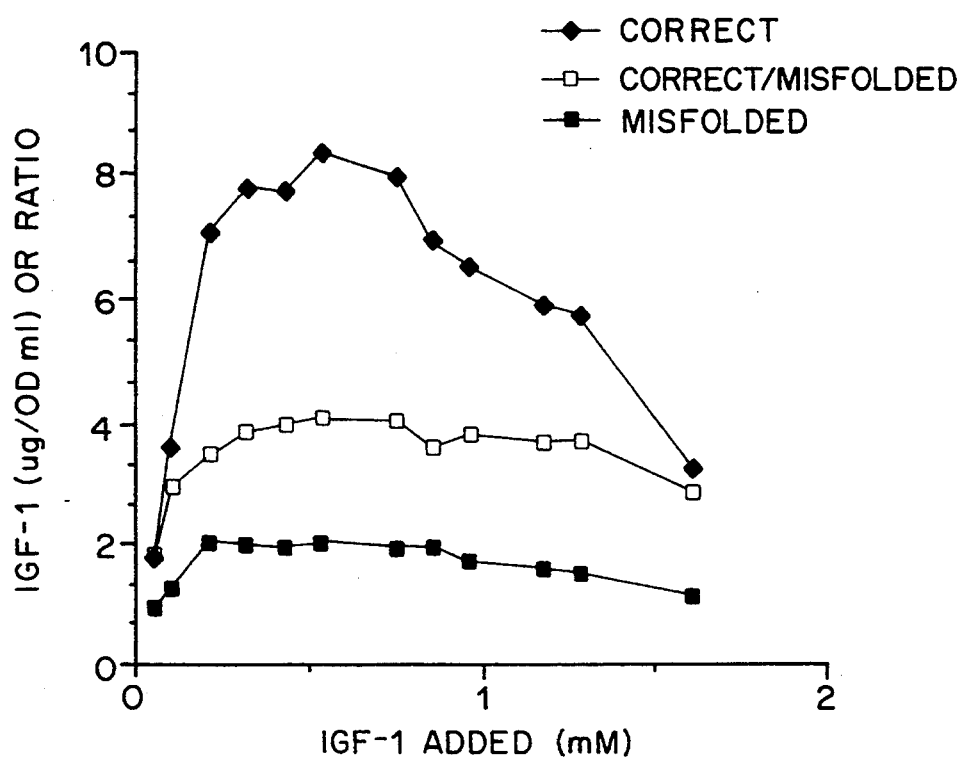
FIG. 12 depicts a graph of resultant IGF-I titer as a function of the concentration of IGF-I present, with a constant IGF-I/DTT ratio.

In a separate determination of the effect of IGF-I concentration on folding (with constant IGF-I/DTT), the results shown in FIG. 12 were obtained, indicating an optimum IGF-I concentration for optimum yield corresponding to 1.5 to 5 mg/ml (approximately 0.2 to 0.7 mM).

B. Altering incubation temperature

Refractile body protein was obtained as described above and solubilized in acetate buffer containing 2M urea and 2 mM DTT. Refolding was allowed to proceed 4 hours at various temperatures. Refolding at 4° C. reduced RIA titers 50% compared to 23° C. or 37° C. See Table 4.

TABLE 4

| Effect of Temperature | | |
|---|---|---|
| Temperature (°C.) | Solubility | IGF-I RIA (μg/ml OD) |
| 4 | ++++ | 4.60 |
| 23 | ++++ | 9.14 |
| 37 | ++++ | 8.66 |

In a separate experiment where the folding was done in CAPSO buffer, pH 10.5 in the presence of 20% methanol, the amount of correct IGF-I obtained was optimized between 15° and 37° C. See Table 5.

TABLE 5

| Effect of Temperature | | | |
|---|---|---|---|
| Temperature (°C.) | Correct IGF-I (μg/OD ml) | Correct/ Misfolded | Methionyl Sulfoxide* (%) |
| 4 | 10.6 | 2.5 | 2.6 |
| 15 | 17.8 | 3.7 | 2.2 |
| 23 | 18.2 | 3.9 | 2.1 |
| 37 | 15.3 | 5.1 | 3.1 |

*% of methionyl sulfoxide as compared to correct IGF-I level.

C. Altering incubation time

When the temperature was kept at 23° C. and the time interval varied, with pH 8.2, using intervals of ½, 1, 2, 3, 4, 5, and 24 hours, RIA titers increased with time, reaching a plateau at about 5 hours. See FIG. 13A. In addition, refolding was carried out using CAPSO buffer at pH 10.5 with and without methanol. The data indicated that IGF-I titers (by HPLC assay) increased with time and plateaued. See FIGS. 13B (no methanol) and 13C (with methanol).

D. HPLC profile of refolded refractile body protein

Refolded protein, solubilized as described in Section B above at 23° C. for 4 hours, was examined by HPLC on a reverse-phase Vydac C-18 column at pH 2.0. Two major IGF-I peaks eluted, one co-migrating with authentic IGF-I and the other with a misfolded form in a ratio of 1.5/1 to 5/1. Refractile bodies solubilized in 2M urea and 1–4 mM DTT yield 25–30% of properly folded IGF-I in acetate buffer as determined from the RIA titers, which are a measure of the amount of authentic IGF-I present.

EXAMPLE III

Effects of Various Parameters on Refolding

A. Characterization of refolded IGF-I

Cell lysates were prepared as above through the cell harvesting step. Refractile body protein from a 200 ml-OD cell paste was solubilized in 10 ml of buffer comprising 100 mM NaOAc, pH 8.2, 100 mM NaCl, 2M urea, and 2 mM DTT. Refolding of refractile body protein proceeded 4 hrs at 23° C. The protein was evaluated using preparative reverse-phase HPLC at pH 7.0 on a Waters-C4 column, at pH 7.0. Fractions which co-migrated with authentic IGF-I were subjected to V-8 protease digestion and mass spectrometry analysis.

RIA of the refolded protein revealed an IGF-I titer of 7.9 μg/ml OD. The protein pattern of the refolded sample was compared to that of the refractile body protein prior to refolding, using Coomassie blue-stained 10–20% Tricine gels. Under reduced gel conditions, only one band was visible corresponding to the IGF-I monomer migrating near 6.2 Kd. Under non-reduced gel conditions, bands corresponding to monomer, dimer, and oligomer forms were detected for the refolded but not for the non-refolded sample. Under non-reduced gel conditions, the non-refolded sample contained numerous high molecular weight bands but no band migrating near the 6.2 Kd monomer.

After preparative reverse phase HPLC of the refolded sample, two major IGF-I peaks were obtained. One co-migrated with authentic IGF-I and the other co-migrated with misfolded IGF-I. A significant amount of protein was also found in a regenerate fraction, containing aggregates of IGF-I. When the protein pattern of each of these two major peak fractions was displayed on SDS-Tricine reduced gels, each contained only one band which co-migrated with IGF-I. The distribution of IGF-I, as adduced by the intensity of the stained bands, was approximately 35/25/40 in correctly folded:misfolded:regenerate forms. In non-reduced gels, more than 50% of IGF-I in the regenerate fraction appeared as dimers and oligomers. The results indicate that the correctly folded and misfolded IGF-I exhibit identical mobility in reduced and non-reduced gels and the majority of IGF-I in the regenerate fraction is in a disulfide-linked oligomeric form.

The fractions recovered after HPLC were also analyzed by radioimmunoassay for IGF-I and by bioassay for IGF-I activity. The bioassay measures the ability of the IGF-I to enhance the incorporation of tritiated thymidine, in a dose-dependent manner, into the DNA of BALB/c 3T3 fibroblasts, performed, with some modifications, according to the procedure described by Tamura et al., *J. Biol. Chem.*, 262: 5616–5621 (1989). High IGF-I RIA titers were found only in the fraction co-migrating with correctly folded IGF-I. Similarly, IGF-I activity was high only in that same fraction. See Table 6.

TABLE 6

IGF-I Titers of Various Fractions from HPLC

| Fractions | Co-migrate with | IGF-I titers (μg/ml OD) | |
|---|---|---|---|
| | | RIA | Bioassay |
| 2–13 | | ND* | ND |
| 13–28 | | ND | ND |
| 28–32 | | ND | ND |
| 32–38 | | 0.04 | ND |
| 38–46 | | 0.12 | ND |
| 46–51 | authentic IGF-I | 2.40 | 5.46 |
| 51–55 | misfolded IGF-I | 0.13 | 0.16 |
| 55–58 | regenerate | 0.29 | 1.72 |

*ND is not detectable.

To characterize the disulfide linkage and check the amino acid sequence of refolded protein, the HPLC fractions 46–51, co-migrating with authentic IGF-I, were subjected to V-8 protease digestion and then analyzed by HPLC. The profile is almost identical to that of authentic IGF-I. Several small variant peaks, analyzed further by mass spectroscopy, were identified as incomplete digests of IGF-I fragments. These results indicate that the refolded protein co-migrating with correctly refolded material contained correct disulfide linkages and correct terminal sequences. The refolded protein co-migrating with misfolded protein was similarly analyzed. The results indicated that two of the three disulfide bonds were formed incorrectly.

B. Effect of pH on refolding

Refractile body protein from 4 ml-OD cell pellet was resuspended in 100 μl of NaOAc buffer ranging in pH from 4.1–8.2, all containing 100 mM NaCl, 2M urea, and 2 mM DTT. Solubilization and refolding proceeded for 5 hrs at 23° C. See Table 7.

TABLE 7

Effect of pH on IGF-I Refolding

| pH | Solubility | IGF-I (μg/ml OD) |
|---|---|---|
| 4.1 | – | –0.02 |
| 4.4 | – | 0.03 |
| 5.0 | – | 0.04 |
| 6.0 | + | 0.08 |
| 6.4 | ++ | 0.06 |
| 8.2 | +++ | 5.18 |

Turbidity measurements revealed that the protein was completely insoluble below pH 6.0 and became almost completely soluble at pH 8.2. This was confirmed by soluble protein measurement and PAGE. RIA for IGF-I revealed that correct refolding occurred in a significant amount at pH 8.2 but not at the lower pH values tested.

C. Effect of buffer and pH on refolding

Various buffers were examined at a range of pH within the effective range of each buffer. These buffers and their pKa are: glycylglycine, pKa 8.4, Taps, pKa 8.4, Tris, pKa 8.3, Bicine, pKa 8.3, Tricine, pKa 8.1, Hepes, pKa 7.5, Ampso, pKa 9.0, Ches, pKa 9.3, Capso, pKa 9.6, Amp, pKa 9.7, Caps, pKa 10.4. All buffers contained 100 mM NaCl, 2M urea, and 2 mM DTT. Refractile body protein from 4 ml-OD cell pellet was resuspended in 100 μl of each buffer. Refolding proceeded for 5 hrs at 23° C.

Figure 11A:
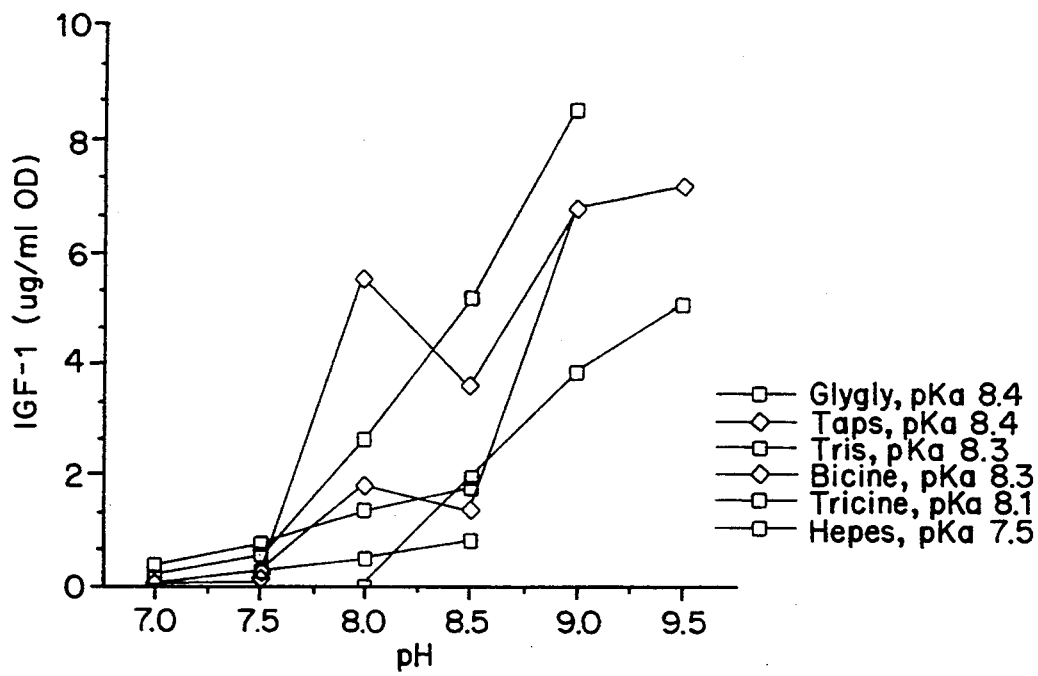
FIGS. 11A and 11B show the effect on IGF-I RIA titers of various pH values and buffers used in solubilizing IGF-I.

Turbidity data, soluble protein measurements, and PAGE indicated that among buffers with slightly basic pKa (pKa 7.5–8.4), solubility of IGF-I increased as the pH increased. At pH 9 and above, almost all IGF-I was solubilized. For Tris, Taps, Bicine, and Glycylglycine buffers, correct refolding, as measured by RIA for IGF-I, increased significantly as pH increased from about 7.5 to 9.5. See FIG. 11A.

Figure 11B:
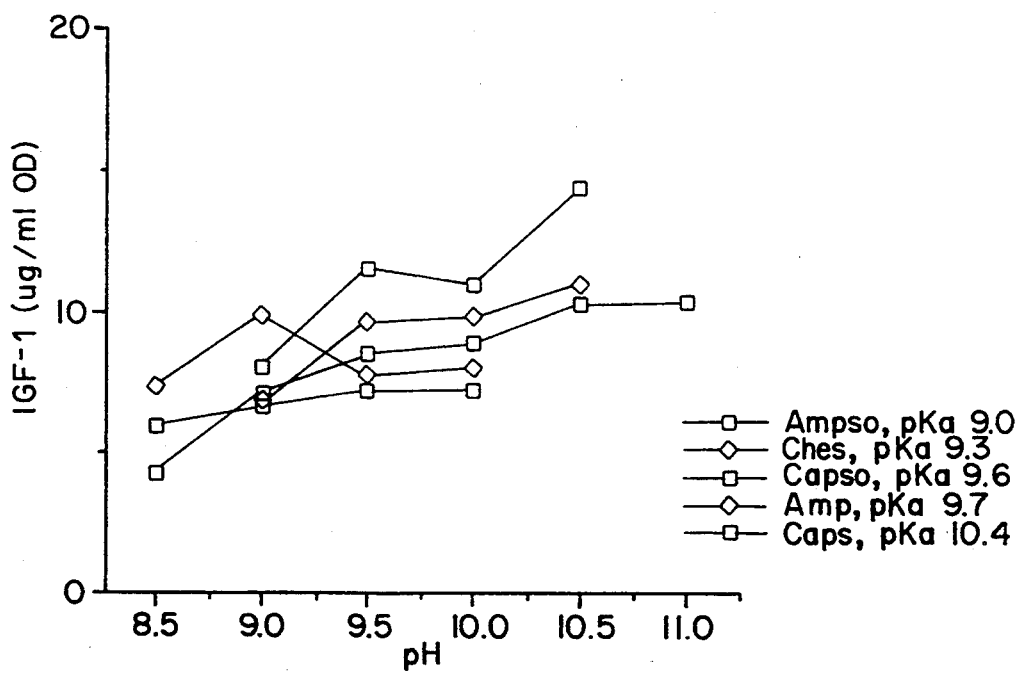
Figure 13A:
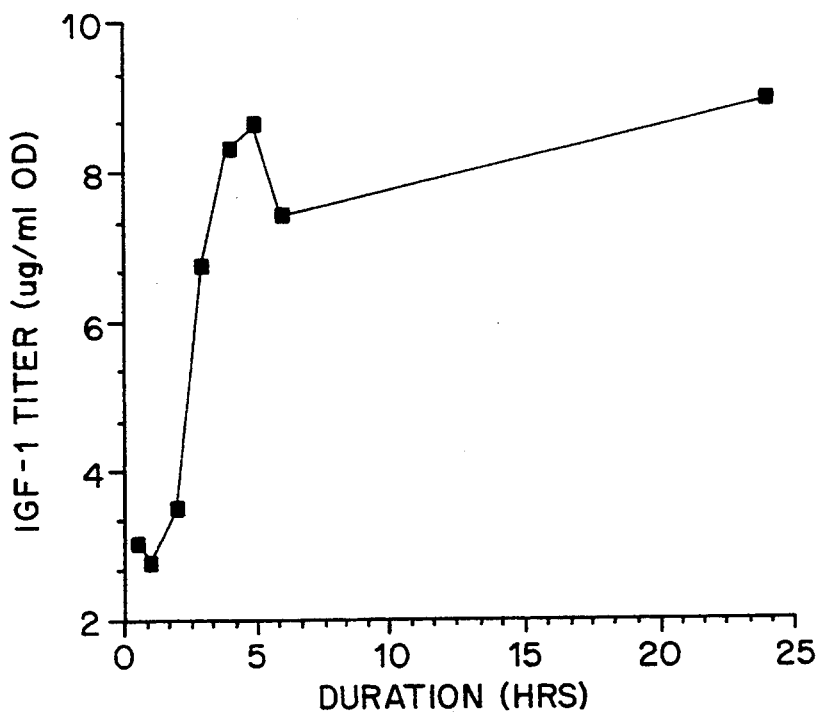
FIGS. 13A, 13B, and 13C show the effect on IGF-I RIA titers of duration time in the solubilizing buffer for refolding, with FIG. 13A using a pH of 8.2 with no methanol, FIG. 13B using a pH of 10.5 with no methanol, and FIG. 13C using a pH of 10.5 with methanol.
Figure 13B:
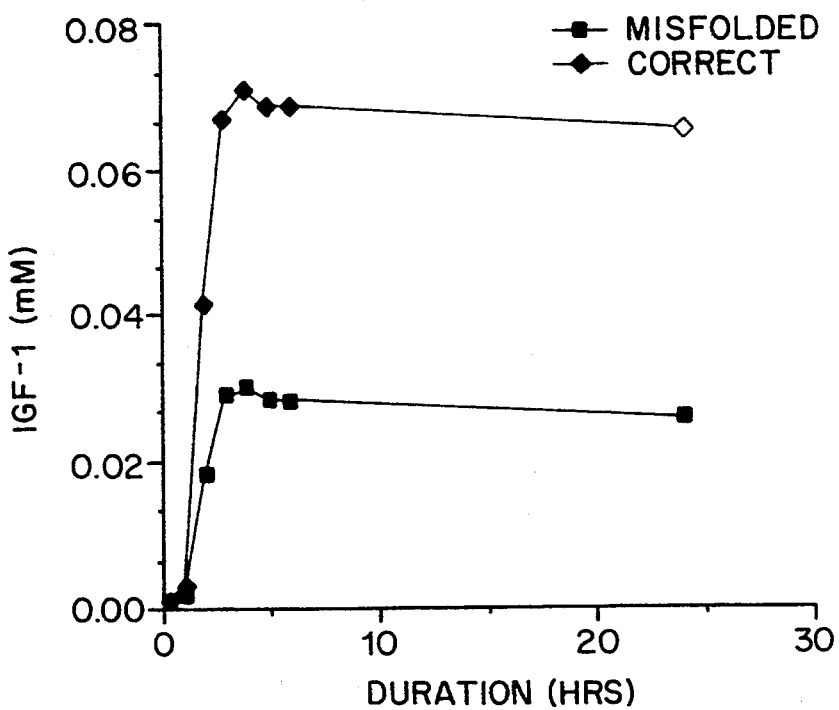
Figure 13C:
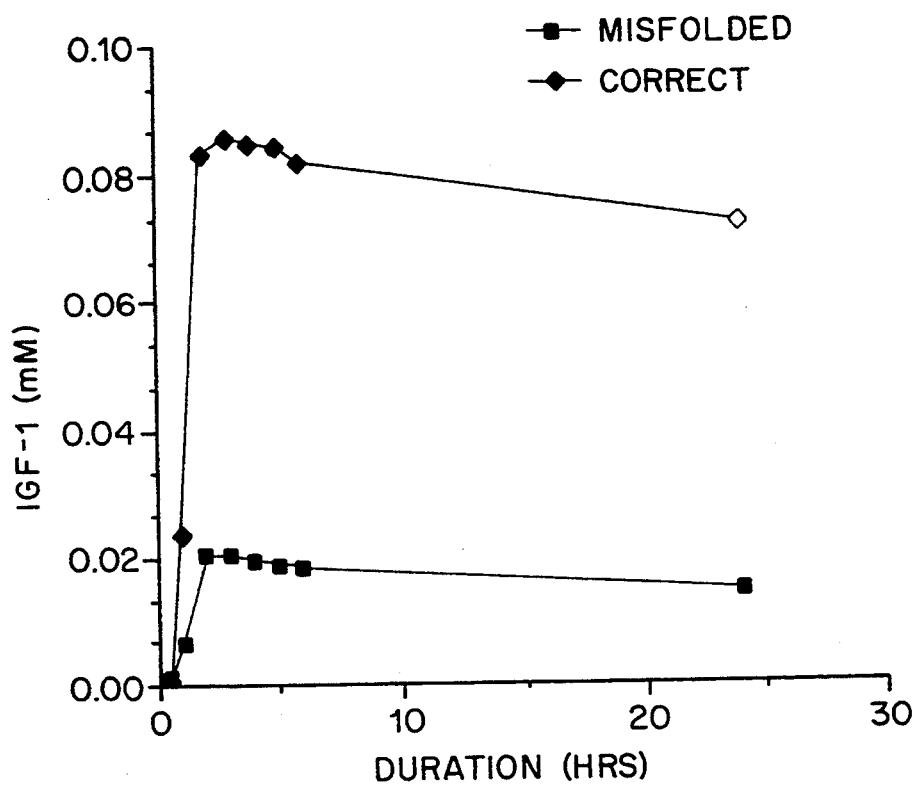

Among buffers with very basic pKa (pKa ≧9.0) IGF-I was almost completely soluble within the useful pH range of these buffers (pH 8.5–11). RIA for IGF-I revealed high titers in all these buffers, for the entire pH range tested. See Fig. 11B. FIGS. 13A-C show a typical time sequence for these reactions.

EXAMPLE IV

Refolding of IGF-I Produced By Various *E. coli* Hosts

Three *E. coli* periplasmic and membrane protease deficient hosts, designated 27A7, 27B4, and 27C7, carrying the IGF-I secretion plasmid pLS32Tsc (described above), were used as a source of refractile body protein. The construction of strains 27A7 and 27C7, is described in Example I. Strain 27B4, which has the complete genotype W3110 tonAΔptr3 phoAΔE15 Δ(argF-lac)169 degP41, was prepared by transducing the degP41 periplasmic protease mutation [Strauch et al., supra] into strain 27A7. This mutation was constructed in vitro by replacing a section of the degP gene with the kanamycin gene to allow for selection of the deletion using kanamycin resistance.

Refractile body protein was isolated from each of these three host strains as previously described from 0.2 g of cell paste in a 5 ml volume. Refractile body protein from a 4 ml-OD cell pellet was resuspended in 100 μl of buffer comprising 100 mM CAPSO, pH 10.5, 100 mM NaCl, 2M urea, and 1-4 mM DTT. Refolding proceeded 5 hrs at 23° C.

During isolation of the refractile body protein, samples were taken to identify the protein distribution from the various hosts. The protein patterns were displayed on Coomassie blue stained reduced SDS gels. For whole cell lysates, approximately 5% and 10% of total protein was IGF-I for the strain 27A7, and for the 27B4 and 27C7, strains, respectively. Supernatant fractions of cell lysates exhibited protein patterns similar to the cell lysates but with a very faint IGF-I band. Pellet fractions (refractile bodies) exhibited IGF-I banding almost exclusively.

IGF-I refolding was measured by RIA. Only the pellet fractions exhibiting an IGF-I band showed significant IGF-I titer in the RIA. The IGF-I titers were highest in the fractions with the darkest staining IGF-I bands, which provides confirmatory data for higher IGF-I concentrations in these fractions. The various *E. coli* hosts and expression levels did not affect the extractability, purity, or refolding of the refractile body proteins. Refractile body proteins from all strains refolded with similar relative yields, as determined from the observation that IGF-I titers correlated well with the intensity of the IGF-I band on the SDS gels.

EXAMPLE V

Measurement of Total IGF-I (correct+misfolded) From Host Cells

Triple-protease deficient *E. coli* cells, as described in Example I (27C7), were extracted in 50 mM Tris buffer, pH 8.0, 6 M urea, 5 mM EDTA, 10 mM DTT. Following centrifugation, the supernatant fraction was eluted through two PLRP-S columns (Polymer Labs Reverse Phase-S) with a linear gradient of 32-45% acetonitrile combined with step gradients. The IGF-I eluted in a peak well separated from those of *E. coli* proteins. The levels of cell-associated and refractile body IGF-I were calculated from peak data as 4.5 g/l and 3.8 g/l respectively. This indicated there is 85% recovery of IGF-I in the refractile body protein preparation.

Cell-associated IGF-I is calculated as 4.7 g/l for a 10-liter fermentation at 100 OD. The IGF-I concentration is approximately 1.5 mg/ml in refractile body protein from a 4 OD-ml *E. coli* cell pellet in 100 μl refolding buffer.

EXAMPLE VI

Effect of Hydrophobic Agents on IGF-I Refolding

Refractile body protein from a 4 OD-ml *E. coli* strain 27C7 cell pellet was refolded in 100 μl of IGF-I refolding buffer consisting of 100 mM CAPSO, pH 10.5, 100 mM NaCl, 2M urea, 2 mM DTT and also containing either 20% ethanol or 20% methanol as hydrophobic agent. See Table 8.

TABLE 8

Effect of Hydrophobic Agents on IGF-I Refolding

| Agent (20% v/v) | Correct (μg/OD ml) | Misfold (μg/OD ml) | Correct/ Misfolded | Increased Yield (%)* |
|---|---|---|---|---|
| Run 1 | | | | |
| — | 12.2 | 5.1 | 2.4 | — |
| Methanol | 17.2 | 4.2 | 4.1 | 20 |
| Run 2 | | | | |
| — | 14.2 | 5.6 | 2.5 | — |
| Methanol | 18.9 | 4.4 | 4.3 | 34 |
| Ethanol | 18.2 | 3.3 | 5.5 | 28 |

*Enhanced by the organic solvent methanol or ethanol.

Refolding proceeded at 23° C. for 5 hours. Addition of methanol or ethanol increased the ratio of correctly folded to misfolded IGF-I and the total yield (correct-+misfolded), measured by peak analysis after HPLC with a Vydac C-18 column. The ratio of correct:misfolded was about 4.1-4.4 and 2.4-2.7 for samples with and without methanol, respectively. The ratios of several more hydrophobic minor IGF-I peaks also changed in the more hydrophobic buffer. It was also discovered that as the percent methanol increases from 0% up to 20%, the ratio of correct:misfolded increases.

EXAMPLE VII

Comparison of β-mercaptoethanol (BME) and DTT as Reducing Agents

Refractile body protein from a 4 OD-ml *E. coli* cell pellet, as described in Example I, was refolded in 100 μl of IGF-I refolding buffer consisting of 100 mM CAPSO, pH 10.5, 100 mM NaCl, 2M urea, and varying concentrations of BME or DTT. Refolding proceeded at 23° C. for 5 hours. The ratio of correct to misfolded conformer and the yield was analyzed by HPLC of the solubilized protein through a Vydac C-18 column. See Table 9. The yield of total IGF-I (both Correct and misfolded) was decreased with BME as reducing agent as compared to DTT as reducing agent at all concentrations. However, the ratio of correct to misfolded conformer was similar with either reagent.

TABLE 9

Effect of BME and DTT on IGF-I Refolding

| Reducing Reagent | Correct IGF-I (μg/OD ml) | Misfolded IGF-I (μg/OD ml) | Ratio Correct/ Misfolded |
|---|---|---|---|
| DTT, 1 mM | 10.1 | 4.9 | 2.1 |
| DTT, 2 mM | 13.7 | 5.9 | 2.3 |
| DTT, 4 mM | 12.1 | 5.4 | 2.3 |
| BME, 1 mM | 8.5 | 3.2 | 2.7 |
| BME, 2 mM | 7.5 | 3.1 | 2.5 |
| BME, 4 mM | 6.2 | 2.8 | 2.3 |

EXAMPLE VIII

Comparison of BME and DTT as Reducing Agents in the Presence of Methanol

Refractile body protein from a 4 OD-ml *E. coli* cell pellet, as described in Example I, was refolded in 100 μl of IGF-I refolding buffer consisting of 100 mM CAPSO, pH 10.5, 100 mM NaCl, 2M urea, 20% methanol, and varying concentrations of BME or DTT as reducing agent. Refolding proceeded 5 hrs at 23° C. The refolded protein was analyzed using a Vydac C-18 HPLC column to separate correct and misfolded forms. At 1 mM, 2 mM, or 4 mM DTT, HPLC of the refolded sample revealed a ratio of correct:misfolded IGF-I of about 4:1. Total yield (correct+misfolded) remained I/DTT ratio (FIG. 15B) or a constant DTT concentration (1 mM for FIG. 15D and 2 mM for Fig. 15C).

TABLE 10

Effect of Refractile Body Particle Concentration on IGF-I Refolding

Figure 14A:
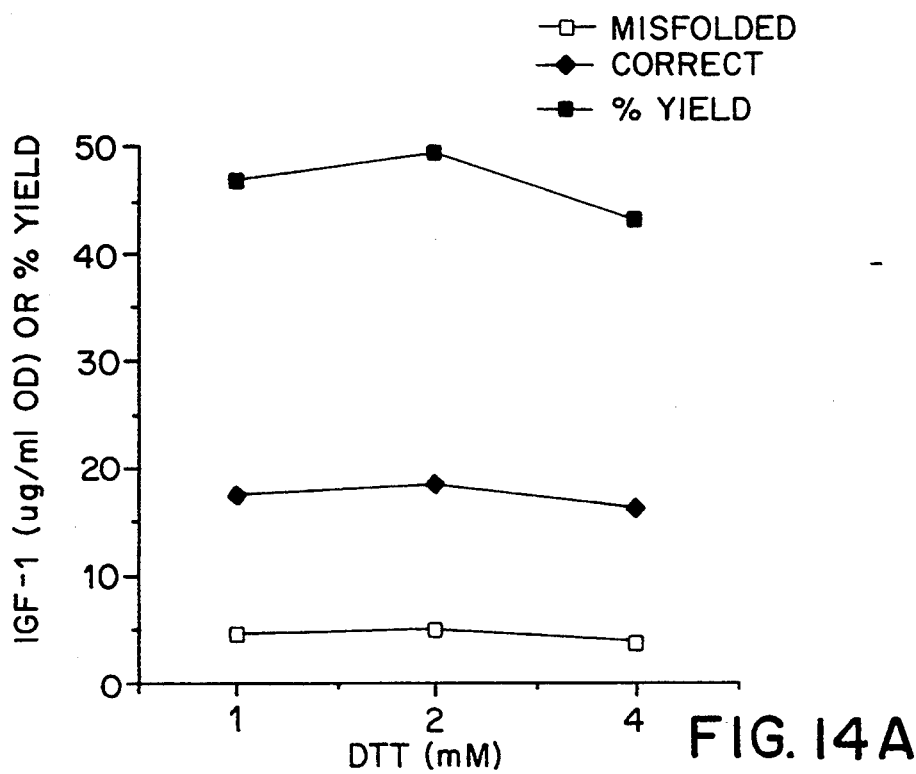
FIGS. 14A and 14B show IGF-I titer and correct::misfolded IGF-I as a function of the concentration of dithiothreitol (DTT) and β-mercaptoethanol (BME), respectively, in the solubilizing buffer.

| RB (OD ml/ 100λ) | DTT (mM) | IGF/ DTT | Sol. IGF (mM) | % Sol. | Correct (µg/OD ml) | Misfold (µg/OD ml) | Ratio Correct/ Misfold |
|---|---|---|---|---|---|---|---|
| 0.10 | 0.05 | 0.11 | 0.01 | 91 | 0.0 | 0.0 | — |
| 0.25 | 0.12 | 0.11 | 0.01 | 90 | 0.0 | 0.0 | — |
| 0.50 | 0.25 | 0.11 | 0.03 | 92 | 3.2 | 1.8 | 1.8 |
| 1.00 | 0.50 | 0.11 | 0.05 | 90 | 3.1 | 1.2 | 2.4 |
| 4.00 | 2.00 | 0.11 | 0.20 | 94 | 9.5 | 2.2 | 4.3 |
| 8.00 | 4.00 | 0.11 | 0.36 | 84 | 9.2 | 2.1 | 4.3 |
| 12.00 | 6.00 | 0.11 | 0.36 | 80 | 8.6 | 1.9 | 4.4 |
| 0.10 | 1.00 | 0.01 | 0.01 | 100 | 0.0 | 0.0 | — |
| 0.25 | 1.00 | 0.01 | 0.01 | 100 | 1.0 | 0.7 | 1.3 |
| 0.50 | 1.00 | 0.03 | 0.03 | 100 | 4.3 | 1.7 | 2.6 |
| 1.00 | 1.00 | 0.05 | 0.05 | 96 | 4.2 | 1.4 | 3.0 |
| 4.00 | 1.00 | 0.22 | 0.20 | 91 | 10.1 | 2.5 | 4.0 |
| 8.00 | 1.00 | 0.43 | 0.03 | 7 | 3.9 | 1.3 | 3.1 |
| 12.00 | 1.00 | 0.65 | 0.05 | 7 | 1.2 | 0.5 | 2.4 |
| 1.00 | 2.00 | 0.03 | 0.05 | 100 | 4.9 | 1.4 | 3.4 |
| 4.00 | 2.00 | 0.11 | 0.21 | 96 | 9.5 | 2.2 | 4.3 |
| 8.00 | 2.00 | 0.11 | 0.21 | 62 | 8.6 | 2.0 | 4.2 |
| 12.00 | 2.00 | 0.32 | 0.05 | 7 | 3.5 | 1.1 | 3.3 | approximately constant regardless of concentration of DTT. See FIG. 14A.

Figure 14B:
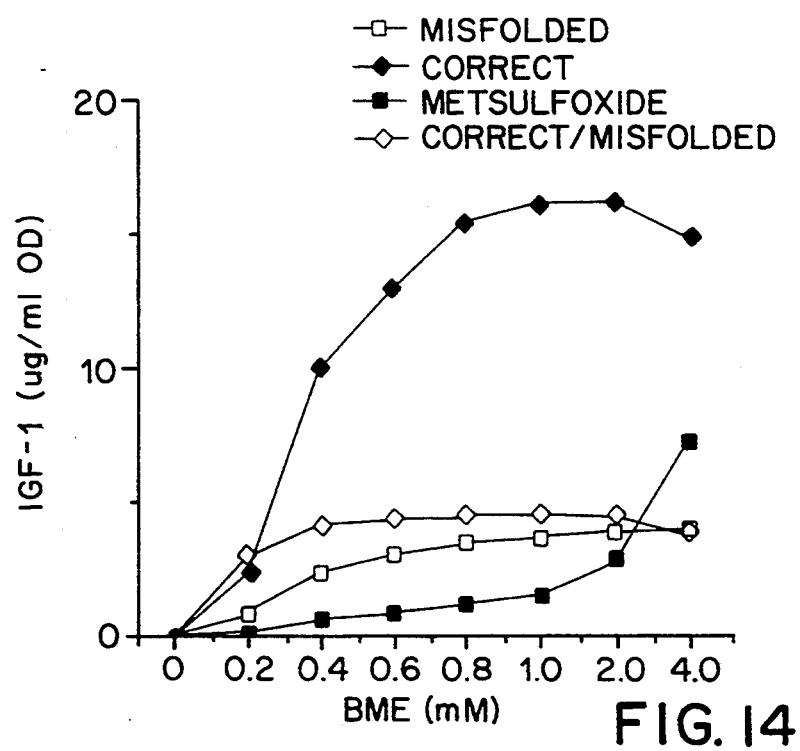

BME was effective in promoting refolding at as low as 0.2 mM concentration. At concentrations above 0.8 mM BME, IGF-I was completely soluble. Three peaks eluted by HPLC were identified as the correct, misfolded, and methionyl sulfoxide conformers. IGF-I refolding was dependent on the concentration of BME, with maximum yield of IGF-I at 1-2 mM BME. The yield is slightly lower (13%) than the maximum yield with DTT. The correct:misfolded ratio was about 3:1 at low BME (0.2 mM) and increased to about 4.2:1 as BME concentration increased to 2 mM. However, levels of the methionine sulfoxide variants also increased with increasing BME concentration. See FIG. 14B.

EXAMPLE IX

Effect of varying IGF-I and DTT Concentrations

Refractile body protein from a 4 OD-ml *E. coli* cell paste, as described in Example 1, was refolded in 100 µl of IGF-I refolding buffer consisting of 100 mM CAPSO, pH 10.5, 100 mM NaCl, 2M urea, 20% methanol, and varying concentrations of DTT. Refolding proceeded 5 hrs at 23° C. The soluble, refolded protein was analyzed using a Vydac C-18 HPLC column to separate correct and misfolded forms. Insoluble protein was solubilized in 100 µl of solution containing 6M urea, 50 mM Tris, pH 8.0, 5 mM EDTA, and 10 mM DTT and analyzed using two PLRP-S columns connected in series. Solubilized protein in the refolding buffer was determined as the difference between total IGF-I protein in the refolding buffer and IGF-I in the pellet, calculated from the PLRP-S analysis. Total IGF-I from refractile body particles from 4 ml-OD cell paste is about 1.5 mg/ml.

Figure 15A:
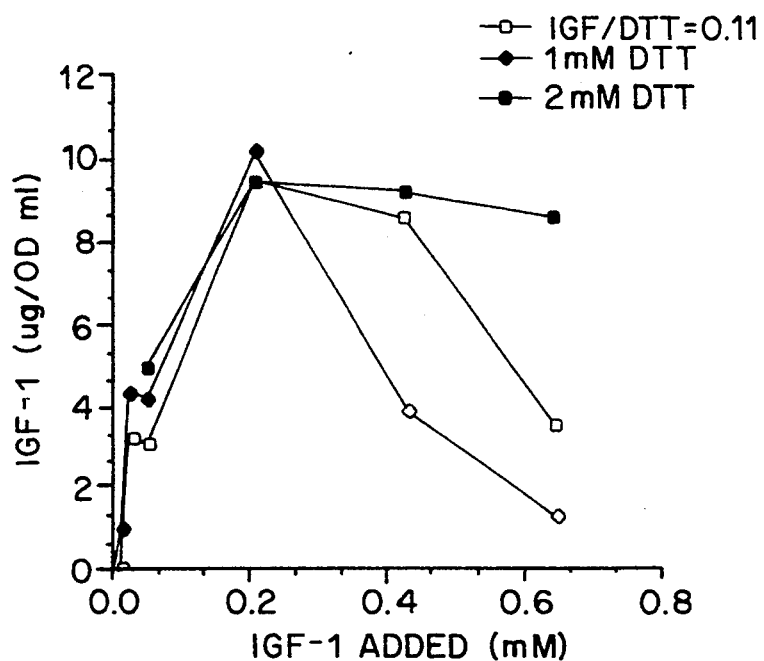
FIG. 15A shows correct IGF-I formation as a function of IGF-I added for IGF-I solubilized using IGF-I/DTT =0.11, 1 mM DTT, and 2 mM DTT.
Figure 15B:
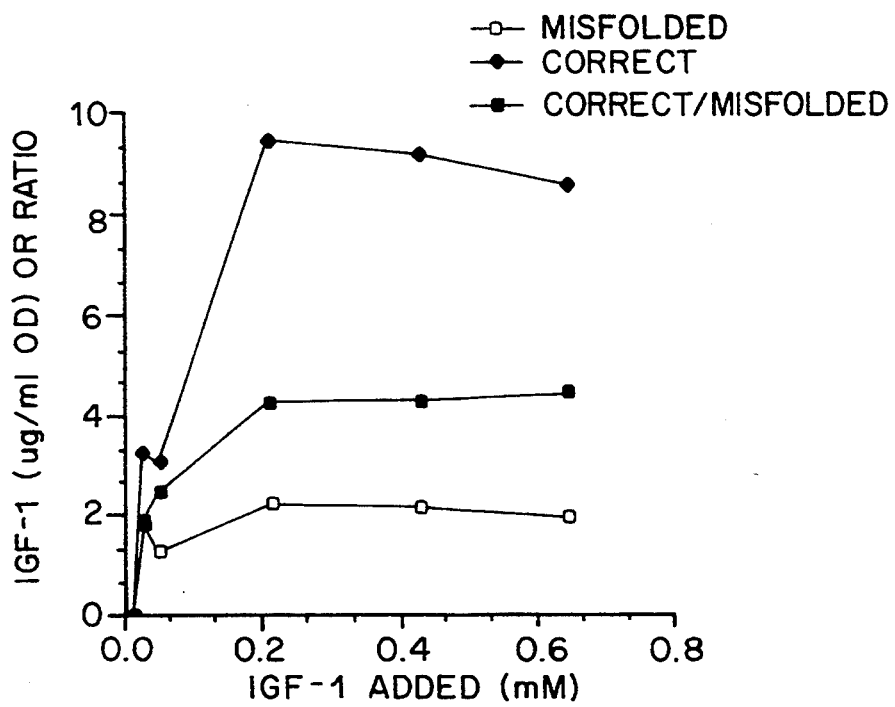
FIGS. 15B, 15C, and 15D show IGF-I titer and correct:misfolded IGF-I as a function of IGF-I added for IGF-I solubilized using a constant IGF-I/DTT =0.11, 2 mM DTT, and 1 mM DTT, respectively.
Figure 15C:
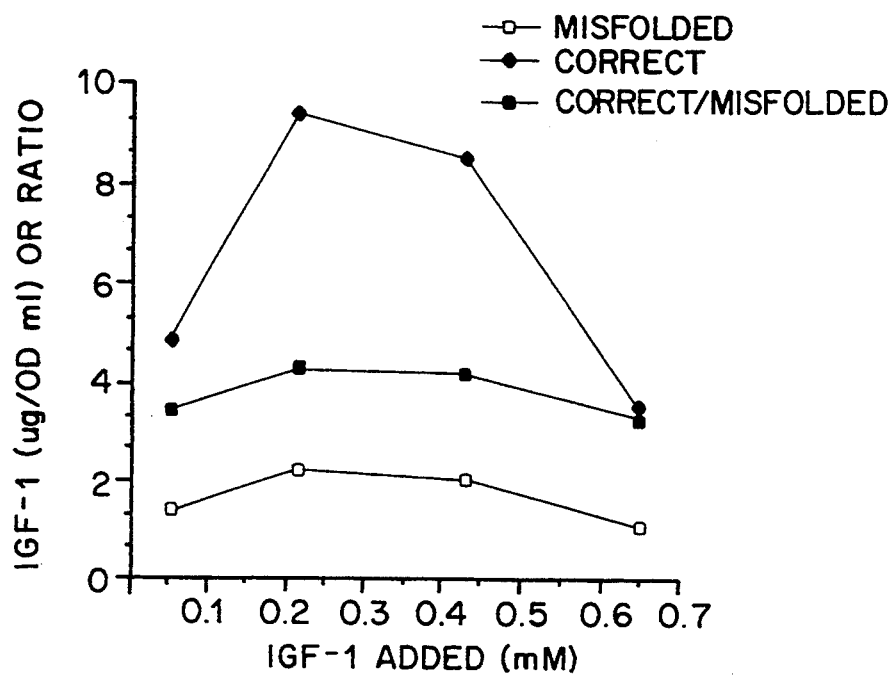
Figure 15D:
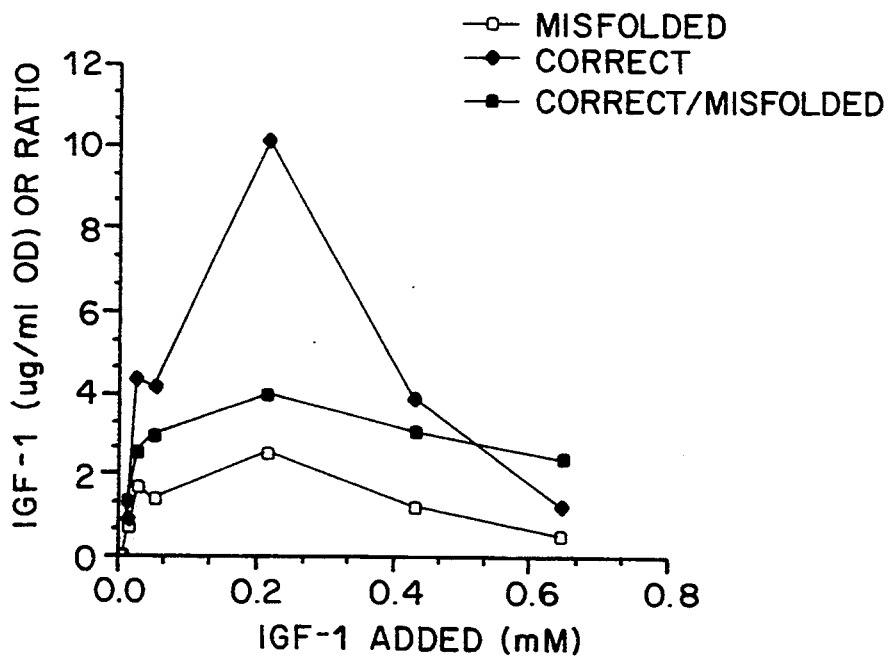

Effects of varying concentrations of DTT and IGF-I refractile body (RB) protein are shown in Table 10 and in FIGS. 15A, 15B, 5C, and 15D, with FIG. 15A showing only correct IGF-I titer for either a single DTT concentration or a constant IGF-I/DTT ratio of 0.11. The other figures show IGF-I titers and ratios of correct to misfolded IGF-I at either a constant IGF- Both the ratio of properly folded to misfolded IGF-I and the yield of properly folded IGF-I increased as the soluble IGF-I concentration was increased to approximately 0.2 mM. Further increases to 0.7 mM (5.3 mg/ml) IGF-I did not significantly decrease either the yield or the properly folded to misfolded ratio. The best yield and ratio were obtained at an IGF-I/DTT ratio of 0.11–0.22.

EXAMPLE X

Effect of Concentrated and Diluted Urea on Folding

Figure 16:
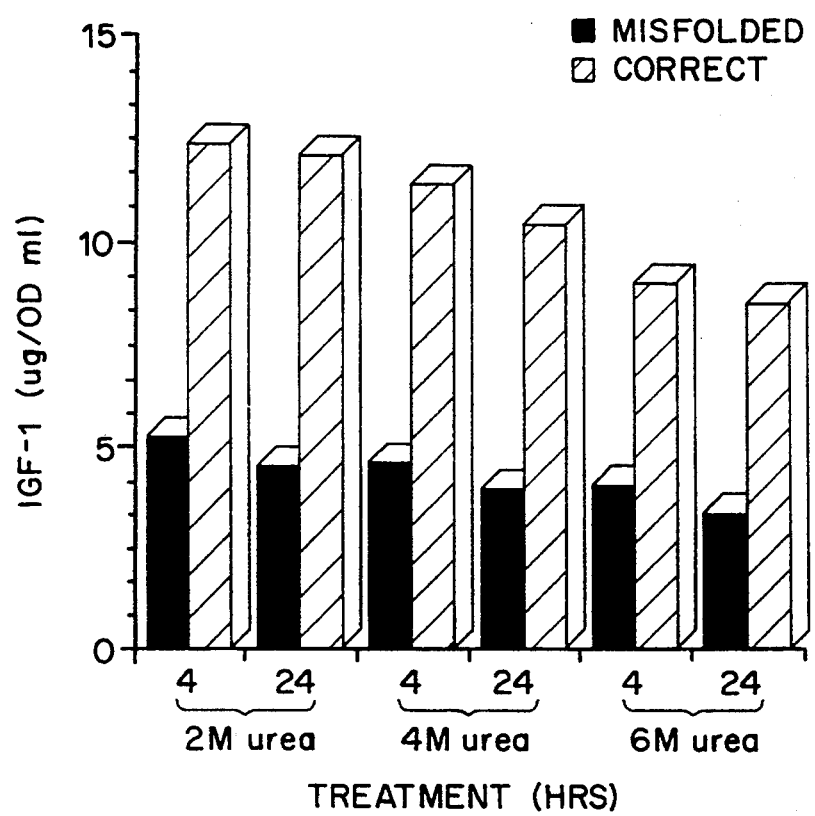
FIG. 16 shows the effect of dilution to 2M urea of more concentrated urea solutions on folding, where the slashed bars are correctly folded IGF-I and the solid black bars are misfolded IGF-I, examining original urea concentrations of 2M, 4M, and 6M at 4 hours (diluted and incubated for another 5 hours) and 24 hours (undiluted).

Refractile body IGF-I protein from a 4 OD-ml *E. coli* cell paste, as described in Example I, was treated with various urea concentrations for 4 hours or 24 hours. The protein to DTT ratio was maintained at 0.11, 20% methanol was added, and the initial protein concentration was increased to be proportional to the initial urea concentration. Four-hour samples were diluted with IGF-I refolding buffer as described in Example IX, except with urea and DTT omitted, to a final urea concentration of 2M. Then they were incubated for an additional 5 hours before IGF-I levels were measured. IGF-I titers were also measured for the 24-hour samples incubated without urea dilution. The results, shown in FIG. 16, indicate that the refolding yield was lower for samples treated with 4M or 6M urea for 4 hours and then diluted and also for samples refolded in 4M or 6M urea for 24 hours (when compared to that obtained with an original 2M urea concentration). For both diluted and undiluted incubations, the refolding yield decreased as the urea concentration increased.

In summary, the results show that insoluble, misfolded IGF-I isolated from prokaryotic cells can be concurrently solubilized and refolded to the correct conformation in a single buffer containing chaotropic agent and reducing agent. To accomplish this, the chaotropic and reducing agents are kept at the minimal respective concentrations that will substantially solubilize the IGF-I. The yield of correctly folded IGF-I improved with the addition of hydrophobic agent to the buffered solution. Optimal solubilization and refolding are obtained with alkaline buffer at a pH range of 7.5–10.5 with about 2M urea and about 2–4 mM DTT or 1–2 mM BME.

Deposit of Material

The following culture has been deposited with the American Type Culture Collection, 12301 Parklawn Drive, Rockville, MD, USA (ATCC):

| Strain | ATCC Dep. No. | Deposit Date |
| --- | --- | --- |
| E. coli 27C7 | 55,244 | October 30, 1991 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty, and subject to an agreement between Genentech, Inc. and ATCC, which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture on deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A process for reactivating insoluble, misfolded IGF-I contained in prokaryotic host cells, which process comprises:
 (a) isolating said IGF-I; and
 (b) incubating said isolated IGF-I in an alkaline buffered solution comprising 1-3M chaotropic agent and the minimal concentration of reducing agent sufficient for solubilization, under conditions of IGF-I concentration and incubation temperature and time whereby solubilization, unfolding, and refolding of the IGF-I all occur during the incubation.

2. The process of claim 1 wherein the IGF-I is isolated from the periplasm of the host cells.

3. The process of claim 1 wherein said buffered solution has a pH of about 7.5-10.5.

4. The process of claim 3 wherein said buffered solution comprises Capso buffer at about pH 8.5-10.5.

5. The process of claim 1 wherein the incubation step is carried out at about 10°-40° C. for about 1 to 24 hours.

6. The process of claim 5 wherein the incubation step is carried out at about 15°-37° C. for about 2 to 12 hours 7. The process of claim 1 wherein said chaotropic agent is urea at 1-3M or guanidine hydrochloride at about 1M.

8. The process of claim 1 wherein said reducing agent is dithiothreitol at about 1-8 mM, β-mercaptoethanol at about 0.2-2 mM, or cysteine.

9. The process of claim 1 wherein said chaotropic agent is urea at about 1.5-2.5M and said reducing agent is dithiothreitol at about 2-4 mM or β-mercaptoethanol at about 1-2 mM.

10. The process of claim 1 wherein said buffered solution additionally comprises a hydrophobic agent.

11. The process of claim 10 wherein said hydrophobic agent is methanol or ethanol.

12. The process of claim 1 wherein step (a) is carried out by treating the host cell culture with a buffered solution of ionic strength sufficient to substantially solubilize the host polypeptides, but not the insoluble, misfolded IGF-I, disrupting the cells to form a soluble fraction and a fraction containing the insoluble, misfolded IGF-I, centrifuging the disrupted cells, and collecting the pellet containing the insoluble, misfolded IGF-I fraction.

13. The process of claim 12 wherein the cells are treated by suspension in the buffered solution at about pH 5 to 9 and at an ionic strength of about 0.01 to 2M.

14. The process of claim 13 wherein the buffered solution in which the cells are suspended is at about pH 6 to 8 and has an ionic strength of 0.1 to 0.2M.

15. The process of claim 1 wherein said host cells are bacterial cells.

16. The process of claim 15 wherein said bacterial cells are *E. coli*.

17. The process of claim 16 wherein the *E. coli* cells are deficient in an endogenous protease.

18. The process of claim 17 wherein the *E. coli* cells are deficient in an endogenous periplasmic protease.

19. The process of claim 18 wherein the *E. coli* cells have the complete genotype of *E. coli* 27C7.

20. The process of claim 1 wherein the chaotropic agent is present in the solution at a concentration of about 1.5-2.5M.

21. A new process for reactivating insoluble, misfolded IGF-I contained in prokaryotic host cells, which process comprises:
 (a) isolating said IGF-I; and
 (b) incubating said isolated IGF-I in an alkaline buffered solution comprising 1-3M chaotropic agent and the minimal concentration of dithiothreitol sufficient for solubilization, under conditions of IGF-I concentration and incubation temperature and time whereby solubilization, unfolding, and refolding of the IGF-I all occur during the incubation.

22. The process of claim 21 wherein the dithiothreitol is at a concentration of about 2-4 mM.

* * * * *